(12) United States Patent
Riley et al.

(10) Patent No.: US 9,931,041 B2
(45) Date of Patent: Apr. 3, 2018

(54) METHOD AND APPARATUS FOR FRACTIONAL FLOW RESERVE MEASUREMENTS

(71) Applicant: BAYER HEALTH CARE LLC, Whippany, NJ (US)

(72) Inventors: Michael A. Riley, Saxonburg, PA (US); Michael A. Spohn, Fenelton, PA (US); Gerald W. Callan, Cranberry Township, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 15/482,947

(22) Filed: Apr. 10, 2017

(65) Prior Publication Data

US 2017/0273572 A1    Sep. 28, 2017

Related U.S. Application Data

(63) Continuation of application No. 15/097,846, filed on Apr. 13, 2016, now Pat. No. 9,615,755, which is a (Continued)

(51) Int. Cl.
*A61B 5/02* (2006.01)
*A61M 25/00* (2006.01)
(Continued)

(52) U.S. Cl.
CPC .......... *A61B 5/02028* (2013.01); *A61B 5/021* (2013.01); *A61B 5/02007* (2013.01); (Continued)

(58) Field of Classification Search
CPC ..... A61B 5/02007; A61B 5/0215; A61B 5/01; A61B 5/02154; A61B 5/02158; (Continued)

(56) References Cited

U.S. PATENT DOCUMENTS

| | | | |
|---|---|---|---|
| 7,313,431 B2 * | 12/2007 | Uber, III | A61B 8/06 128/DIG. 12 |
| 2008/0216846 A1 * | 9/2008 | Levin | A61B 17/22 128/898 |
| 2010/0234698 A1 * | 9/2010 | Manstrom | A61B 5/02028 600/301 |

OTHER PUBLICATIONS

Hau, Fractional flow reserve and complex coronary pathologic conditions, European Heart Journal, 2004, 25, 723-727.*

* cited by examiner

*Primary Examiner* — Bo J Peng
(74) *Attorney, Agent, or Firm* — James L. Kent; David Schramm; James R. Stevenson

(57) ABSTRACT

A method of determining fractional flow reserve (FFR) in a blood vessel having stenosis includes injecting fluid into the blood vessel upstream of the stenosis using a power fluid injector, measuring pressure drop across the stenosis, and calculating FFR from measured pressure drop. The injected fluid may comprise a contrast medium. Further actions may include placing a pressure sensor proximal of the stenosis, injecting fluid into the blood vessel upstream of the stenosis using the power fluid injector, and measuring pressure in the blood vessel proximal of the stenosis. The pressure sensor may then be repositioned to a position distal of the stenosis, fluid may be reinjected into the blood vessel upstream of the stenosis using the power fluid injector, and pressure may be measured in the blood vessel distal of the stenosis.

20 Claims, 26 Drawing Sheets

Related U.S. Application Data continuation of application No. 13/534,864, filed on Jun. 27, 2012, now Pat. No. 9,314,584.

(60) Provisional application No. 61/501,472, filed on Jun. 27, 2011.

(51) Int. Cl.
| | |
|---|---|
| *A61B 5/00* | (2006.01) |
| *A61M 5/00* | (2006.01) |
| *A61B 5/021* | (2006.01) |
| *A61B 5/0215* | (2006.01) |
| *A61M 25/01* | (2006.01) |

(52) U.S. Cl.
CPC ........ *A61B 5/02158* (2013.01); *A61B 5/6852* (2013.01); *A61B 5/743* (2013.01); *A61B 5/7475* (2013.01); *A61M 5/007* (2013.01); *A61M 25/00* (2013.01); *A61M 2025/0002* (2013.01); *A61M 2025/0183* (2013.01)

(58) Field of Classification Search
CPC ..... A61B 5/145; A61B 5/02028; A61B 5/021; A61M 5/007; A61M 25/0067; A61M 25/007; A61M 25/0029; A61M 2025/0183; A61M 2025/0002; A61M 2025/0034; A61M 2025/0037
See application file for complete search history.

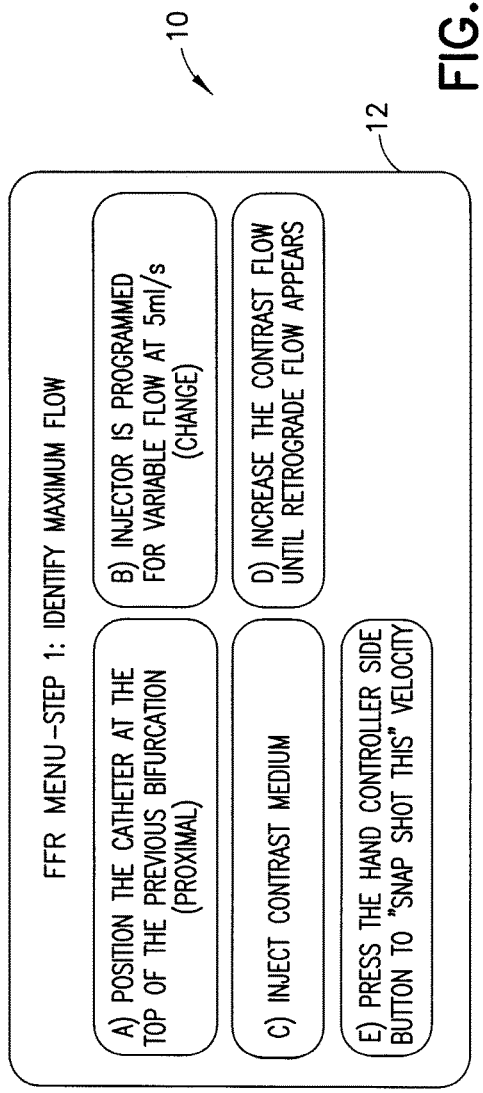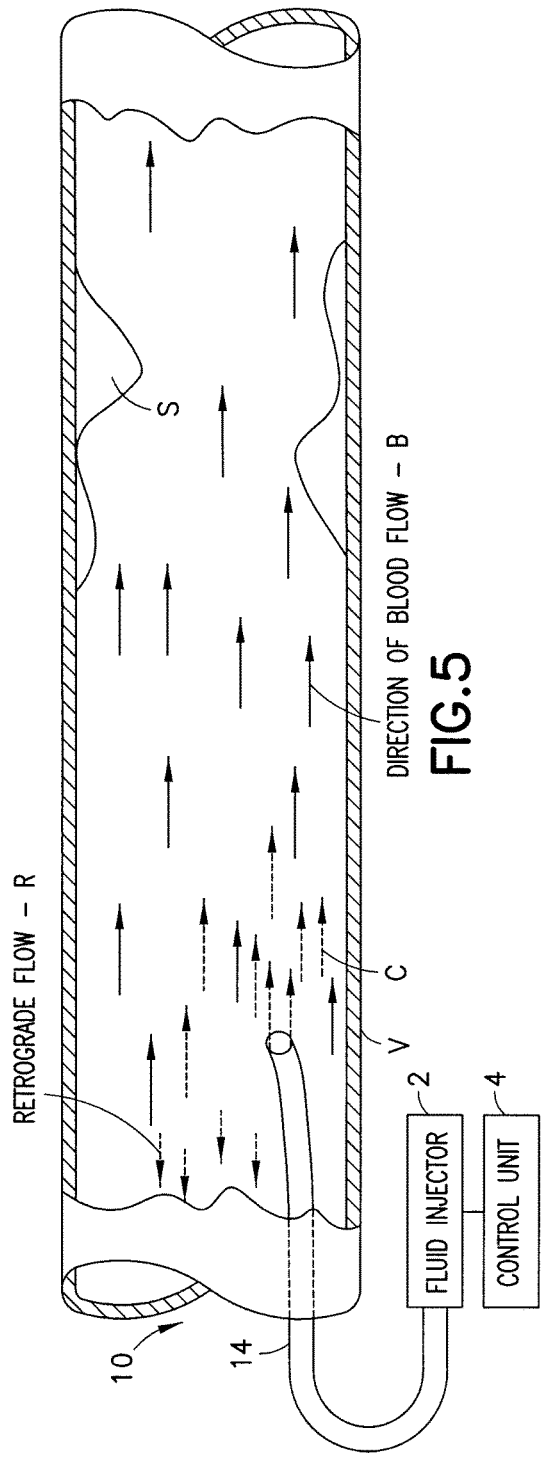

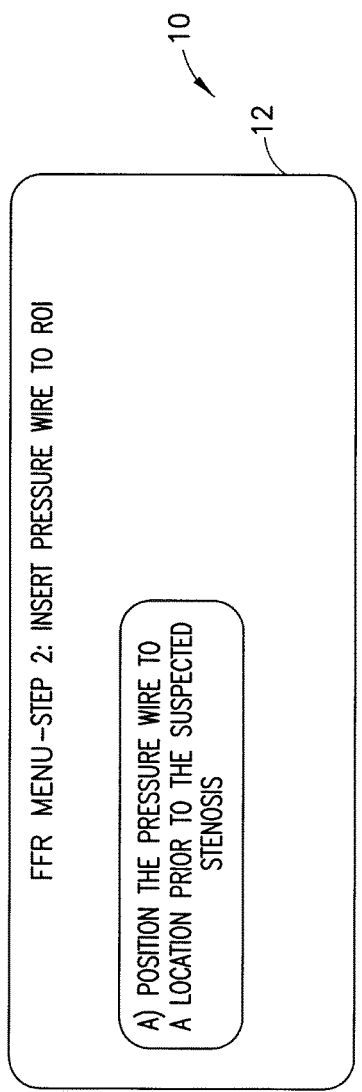

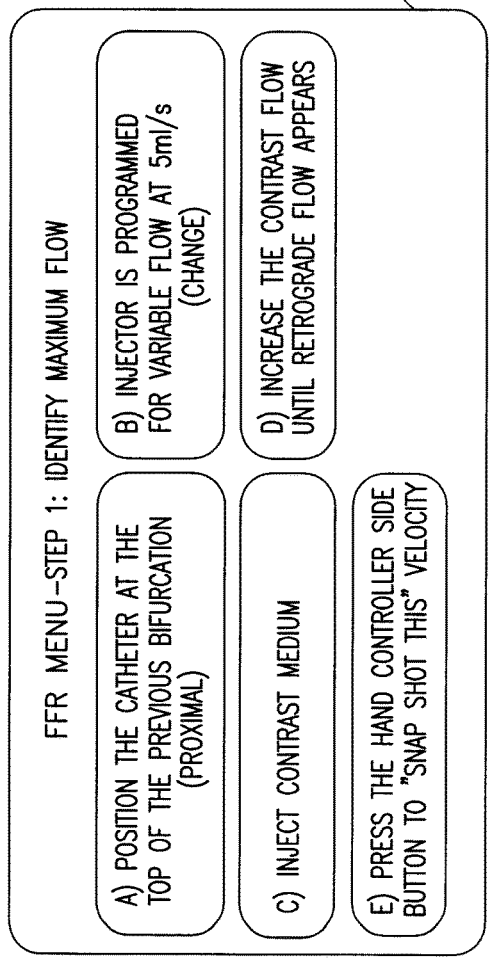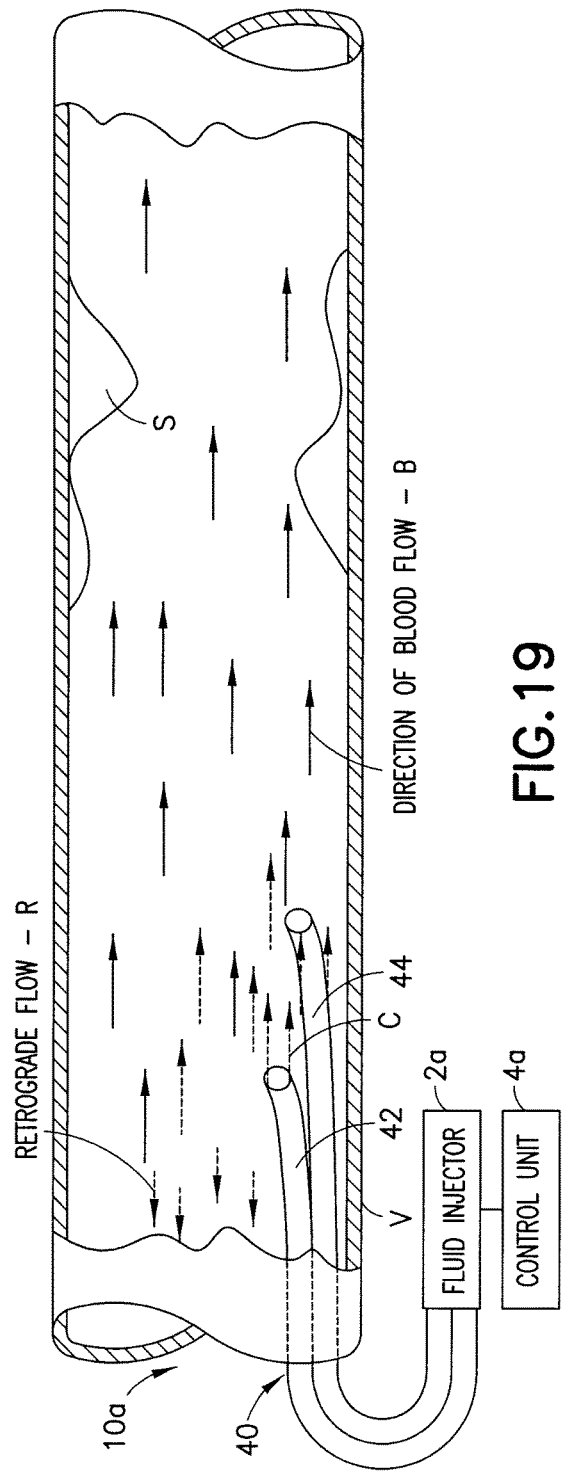
FIG.18
FIG.19

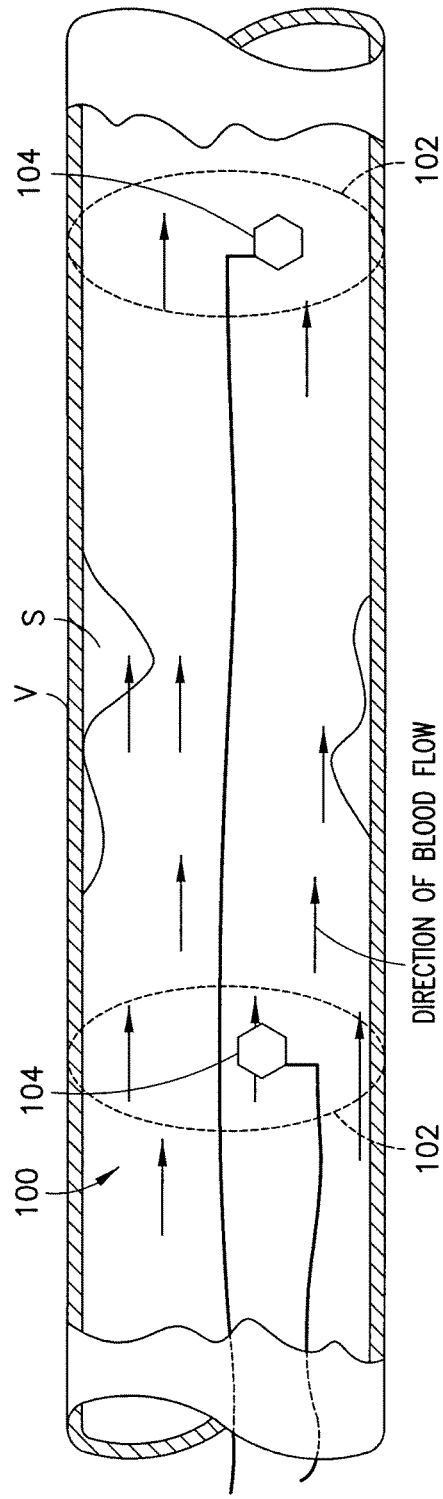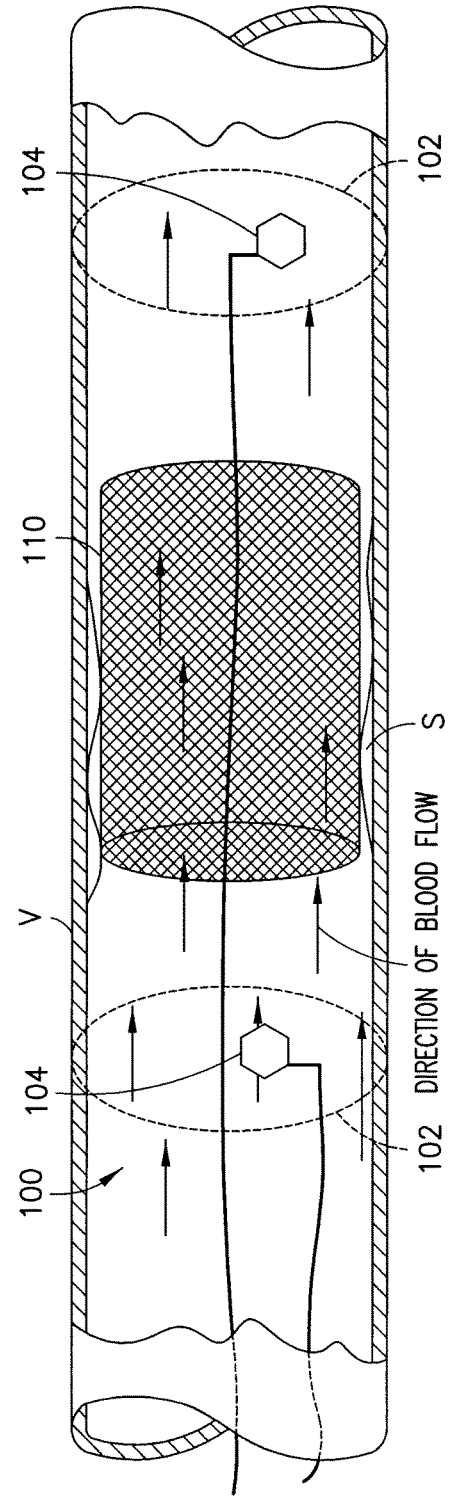

THEORETICAL FFR VALUE WITH BLOOD AND CONTRAST AND TRANSFORM FUNCTION

METHOD AND APPARATUS FOR FRACTIONAL FLOW RESERVE MEASUREMENTS

CROSS-REFERENCE TO RELATED APPLICATION

This application is a continuation of U.S. application Ser. No. 13/534,864, filed Jun. 27, 2012, which claims the benefit of U.S. Provisional Application No. 61/501,472, filed Jun. 27, 2011, and entitled "Method and Apparatus for Fractional Flow Reserve Measurements," the disclosures of each of which are incorporated herein by this reference.

BACKGROUND

Field

The present disclosure is directed to methods and apparatus for determining fractional flow reserve (FFR) which is a method of identifying the effect of an occlusion on blood flow in vasculature. Occlusions could result from a buildup of plaque, a thrombus, or any other material that prevents normal or optimal blood flow.

Description of Related Art

Occlusions in vasculature can be the result of the buildup of plaque, a thrombus, or any other material that prevents normal or optimal blood flow. Vascular diseases are often manifested by reduced blood flow due to atherosclerotic occlusion of vessels. For example, occlusion of the coronary arteries supplying blood to the heart muscle is a major cause of heart disease. Numerous methods are currently available for treating various lesion types, such as percutaneous transluminal angioplasty (PTCA), cutting balloon angioplasty, directional coronary atherectomy (DCA), rotational coronary atherectomy (RCA), ultrasonic breaking catheter angioplasty, transluminal extraction catheter (TEC) atherectomy, rotablator atherectomy, and excimer laser angioplasty (ELCA). Often, stents are placed within the lesion so as to prevent re-closure of the vessel (also known as recoil).

Lesion characteristics, together with vessel condition proximal and distal to the lesion and vascular bed condition, are used to determine the medically and economically optimal treatment method or combination of methods of choice. Geometry, pressure, and flow are three variables often measured in the cardiovascular system. These measurements are performed prior to, during, and after the treatment, providing diagnostic and therapeutic data. The measurement prior to the treatment allows careful treatment selection. Measurements during and after the treatment enable evaluation of the treatment efficacy.

Lesion geometry is evaluated by angiography, qualitative coronary angiography (QCA), or by intravascular ultrasound (IVUS). These measurements allow calculation of the percent diameter stenosis (angiography or QCA) or percent area stenosis (IVUS). This information is used to estimate stenosis severity, but clinicians have realized that direct physical information about pressure and flow is necessary for complete evaluation of coronary artery disease. Physiological measurements such as pressure gradient have been clinically used as an indicator for lesion severity. However, previous attempts to relate the pressure gradient across the stenosis to its functional significance have been disappointing without the use of a pharmacological agent, such as a vasodilator, that artificially increases heart rate. The decrease in the pressure gradient after PTCA has been used to assess the success of the treatment, with poor correlation. Thus, the use of a vasodilator to increase flow rate has been an important component of the foregoing measurement calculations.

Other parameters have been defined and proven more effective as indicators for lesion severity. The coronary flow velocity reserve (CFVR) is defined as the ratio of hyperemic to baseline flow velocity. The fractional flow reserve (FFR) is defined as the ratio of distal (to stenosis) pressure (Pd) to aortic pressure (Pa) during hyperemia. Hyperemic conditions are obtained by administration of vasodilators (e.g., papaverine, adenosine). Clinical studies have demonstrated that, in most cases, lesions with CFVR<2 must be treated using one of the previously mentioned methods, whereas for patients with CFVR>2, angioplasty may be avoided. Similarly, in many cases interventions, such as angioplasty, may be avoided if FFR>0.75. Coronary flow occurs essentially during diastole while systolic contribution to total coronary flow is smaller. A notable difference between diastolic to systolic velocity ratio (DSVR) was observed between normal and stenotic arteries.

The FFR and CFVR are independent but complementary indicators. The first characterize the specific lesion whereas the second is a more global parameter, characterizing the lesioned vessel (lesion and distal bed). Clinical studies (Di Mario et al., Catherization and Cardiac Diagnosis 38, 189-201, 1996) show that for approximately 75% of the patients, CFVR and FFR lead to the same conclusion regarding the lesion significance. At the same time, for 25% of the patients, the conclusions regarding lesion significance were different. This means that simultaneous determination of coronary flow reserve and fractional flow reserve is important and gives the clinician the additional and more complete information regarding the lesion severity.

Technical progress has been made recently with respect to pressure and velocity monitoring guide wires. For example, 0.014" PressureWire® (Radi Medical System, Uppsala, Sweden) is now available for intracoronary pressure measurements. Another maker of pressure wires is Volcano Corporation and sold under the trade name FloWire®. Additionally, these measurements may be performed using diagnostic low profile catheters, Millar pressure transducer catheters (available by Millar Instruments, Inc., Houston, Tex., U.S.A.), or any other intravascular pressure equipment.

A 0.014" doppler flow wire (Cardiometrics Inc., Mountain View, Calif.) is also available for intracoronary velocity measurements. These wires may be advanced into distal parts of the coronary tree without significantly impeding the flow. Simultaneous measurements of FFR and CFVR require the use of both wires and/or a wire with multiple sensors. Such a procedure is complicated, expensive, and used only for research purposes. Therefore, clinicians use either velocity measurements to calculate coronary flow velocity reserve (CFVR) or pressure measurements to calculate fractional flow reserve (FFR). Furthermore, the flow wire is sensitive to the location of the tip within the vessel cross section. The wire tip will measure accurately if located along the longitudinal axis. However, significant errors will appear once the wire is within the boundary layer. Therefore, manipulating the flow wire requires high expertise and a lot of experience. Fortunately, these limitations are not relevant to the pressure wire measurements, yielding accurate data with simple handling.

Relevant United States patents and publications in the field of methods and apparatus for determining fractional flow reserve (FFR) in blood vessels include U.S. Pat. No. 6,089,103 to Smith; U.S. Pat. No. 6,354,999 to Dgany et al.; U.S. Pat. No. 6,471,656 to Shalman et al.; U.S. Pat. No.

6,565,514 to Svanerudh et al.; U.S. Pat. No. 6,615,667 to Smith; U.S. Pat. No. 6,672,172 to Tulkki et al.; U.S. Pat. No. 6,754,608 to Svanerudh et al.; U.S. Pat. No. 7,454,244 to Kassab et al.; U.S. Pat. No. 7,775,988 to Pijls, each incorporated herein by reference in their entirety for this purpose. U.S. Patent Application Publication No. 2009/0234231 to Knight et al. and International Publication No. WO 2010/033971 to Kassab likewise are directed to known methods and apparatus for determining fractional flow reserve (FFR) in a blood vessel and are incorporated herein by reference in their entirety for this purpose.

SUMMARY

In one desirable embodiment, an Avanta™ power injector provided as part of an Avanta™ Fluid Management Injection System manufactured by Medrad®, Inc. comprises an FFR measurement mode or capability. This mode or capability provides a clinician with the ability to achieve and identify a maximum flow rate for FFR measurement without using a vasodilator. Additionally, the FFR measurement mode or capability may instruct the clinician on how to operate the device to capture the greatest pressure difference in the presence of a maximum flow rate. Thus, in a first pressure measurement technique or procedure, supported by the Avanta™ Fluid Management Injection System, an FFR software mode is provided and no disposable or hardware changes are required in the Avanta™ Fluid Management Injection System. The FFR modification only involves changes to the software control system. In a second measurement technique discussed in detail herein, simultaneous pressure measurements of an occlusion or stenosis are taken. This alternative system, technique, or procedure allows for two sensing systems to quantify the effect of an occlusion on blood flow in a single measurement.

The various embodiments described in this disclosure may be used to identify the presence of a stenosis with traditional angiography and then quantify the lesion with saline or other harmless fluid. A dual syringe power injector may also be used in the various embodiments of this disclosure, such as the dual syringe power injector disclosed in International Application No. PCT/US2010/042501 bearing International Publication No. WO 2011/011346 A1, incorporated herein by reference in its entirety.

This disclosure also provides multiple embodiments for taking pressure measurements in a blood vessel. In one embodiment, a pressure sensing arrangement for acquiring simultaneous proximal and distal pressure readings across the stenosis comprises a guide wire supporting optical sensors and micro-electromechanical systems (MEMS) based sensors. In another embodiment, a pressure sensing arrangement for acquiring simultaneous proximal and distal pressure readings across the stenosis comprises implantable support rings for supporting pressure sensors and the like, proximal and distal of the stenosis. In another embodiment, a pressure sensing arrangement for acquiring simultaneous proximal and distal pressure readings across the stenosis comprises an implantable stent for supporting pressure sensors and the like, proximal and distal of the stenosis. In a further embodiment, a pressure sensing arrangement for acquiring simultaneous proximal and distal pressure readings across the stenosis comprises an umbrella or inferior vena cava (IVC) filter for supporting pressure sensors and the like, proximal and distal of a stenosis.

Often an occlusion or stenosis occurs in a bifurcation in a blood vessel, and a multi-pressure wire arrangement is described herein for determining pressure proximal and distal of the stenosis. The multi-pressure wire arrangement may alternatively comprise one or more optical sensors, such as four (4) optical sensors or MEMs based sensors, for determining pressure proximal and distal of the stenosis. In another embodiment, multiple hemodynamic catheters or hemodynamic pressure transducers may be used to determine pressure proximal and distal of a stenosis at a bifurcation in a blood vessel. In a further embodiment, a combination of pressure wires and hemodynamic catheters may be used to determine pressure proximal and distal of a stenosis at a bifurcation in a blood vessel. Additionally, a thrombus removal catheter comprising pressure sensors may be used to determine pressure proximal and distal of a stenosis in a blood vessel.

One method of determining fractional flow reserve (FFR) in a blood vessel having stenosis comprises injecting fluid into the blood vessel upstream of the stenosis using a power fluid injector, measuring pressure drop across the stenosis, and calculating FFR from measured pressure drop. The injected fluid may comprise a contrast medium.

Additional parts of the method may comprise placing a pressure sensor proximal of the stenosis, injecting fluid into the blood vessel upstream of the stenosis using the power fluid injector, and measuring pressure in the blood vessel proximal of the stenosis. Injecting fluid into the blood vessel may be reduced, limited, or discontinued when retrograde flow is present in the blood vessel. Injecting fluid into the blood vessel may be reduced, limited, or discontinued after a preset period of time or after a pressure measurement has been taken.

Further parts of the method may comprise repositioning the pressure sensor to a position distal of the stenosis, reinjecting fluid into the blood vessel upstream of the stenosis using the power fluid injector, and measuring pressure in the blood vessel distal of the stenosis. Reinjecting fluid into the blood vessel may be reduced, limited, or discontinued when retrograde flow is present in the blood vessel. Reinjecting fluid into the blood vessel may be reduced, limited, or discontinued after a preset period of time or after a pressure measurement has been taken. Measuring pressure drop across the stenosis may comprise calculating the ratio of distal pressure to proximal pressure in the blood vessel. The FFR result may be displayed on a user interface display associated with the power fluid injector.

In another embodiment, a method of determining fractional flow reserve (FFR) in a blood vessel having stenosis comprises inserting a multi-lumen catheter into the blood vessel, injecting fluid into the blood vessel upstream of the stenosis using a power fluid injector, measuring pressure drop across the stenosis, and calculating FFR from the measured pressure drop. The injected fluid may comprise a contrast medium. The multi-lumen catheter may comprise at least a fluid injecting or conducting lumen and a hemodynamic monitoring lumen.

The method may further comprise placing a pressure sensor proximal of the stenosis, injecting fluid into the blood vessel upstream of the stenosis using the power fluid injector, and measuring pressure in the blood vessel proximal of the stenosis. Injecting fluid into the blood vessel may be reduced, limited, or discontinued when retrograde flow is present in the blood vessel. Injecting fluid into the blood vessel may be reduced, limited, or discontinued after a preset period of time or after a pressure measurement has been taken. Measuring pressure in the blood vessel proximal of the stenosis may comprise substantially simultaneously measuring pressure using the pressure sensor and a hemodynamic monitoring port on the multi-lumen catheter. Additional parts of the method may comprise repositioning the pressure sensor to a position distal of the stenosis, reinjecting fluid into the blood vessel upstream of the stenosis using the power fluid injector, and substantially simultaneously measuring pressure in the blood vessel distal of the stenosis using the pressure sensor and proximal of the stenosis via a hemodynamic monitoring port on the multi-lumen catheter. Reinjecting fluid into the blood vessel may be reduced, limited, or discontinued when retrograde flow is present in the blood vessel. The step of reinjecting fluid into the blood vessel may be reduced, limited, or discontinued after a preset period of time or after a pressure measurement has been taken.

Further parts of the method may comprise repositioning the pressure sensor to a position proximal of the stenosis, reinjecting fluid into the blood vessel upstream of the stenosis using the power fluid injector, and substantially simultaneously measuring pressure in the blood vessel proximal of the stenosis using the pressure sensor and the hemodynamic monitoring port on the multi-lumen catheter. Injecting fluid into the blood vessel may be reduced, limited, or discontinued when retrograde flow is present in the blood vessel. Injecting fluid into the blood vessel may be reduced, limited, or discontinued after a preset period of time or after a pressure measurement has been taken. Measuring pressure drop across the stenosis may comprise calculating the ratio of distal pressure to proximal pressure in the blood vessel. The FFR result may be displayed on a user interface display associated with the power fluid injector.

Further details and advantages of the various embodiments described in detail herein will become clear upon reviewing the following detailed description of the various embodiments in conjunction with the accompanying drawing figures, where like parts are designated by like reference numerals throughout.

BRIEF DESCRIPTION OF THE DRAWINGS

FIG. 4 is a view of the user interface display for a power injector showing an FFR menu and a first step for determining FFR comprising identifying maximum flow rate in the blood vessel of FIG. 3.

FIG. 5 is a schematic view of the blood vessel with the stenosis of FIG. 3 and showing a maximum flow rate in the blood vessel.

FIG. 6 is a view of the user interface display for a power injector showing an FFR menu and a second step for determining FFR comprising inserting a pressure wire into the blood vessel of FIG. 3.

FIG. 7 is a schematic view of the blood vessel with the stenosis of FIG. 3 and showing a pressure wire inserted into the blood vessel.

FIG. 18 is a view of the user interface display for a power injector showing an FFR menu comprising identifying maximum flow rate in the blood vessel of FIG. 17.

FIG. 19 is a schematic view of the blood vessel with the stenosis of FIG. 17 and showing a maximum flow rate in the blood vessel.

FIG. 28 is a schematic view of a blood vessel with a stenosis and showing implantable support rings for supporting pressure sensors and the like, proximal and distal of the stenosis.

FIG. 29 is a schematic view of a blood vessel with the stenosis of FIG. 28 showing the implantable support rings proximal and distal of the stenosis and a stent disposed between the support rings.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

In this disclosure, various embodiments of a method and system are provided that use a power injector to push fluid through a blood vessel while making an FFR measurement. Conventional FFR practice involves administering a pharmaceutical known as a vasodilator to a patient. This drug increases blood flow across a measured area by pacing the heart to increase cardiac output. Based on this increase, the pressure differential is measured through increases using one or a plurality of sensors. Instead of increasing the pacing of the heart, injecting fluid at a controlled rate using a power injection normalizes pressures to a maximal amount that a particular vessel can support as identified through retrograde flow R in the Figures. The use of a power injector also provides the capability to ensure protocol-based or maximized pressure differential across a lesion.

Figure 1:
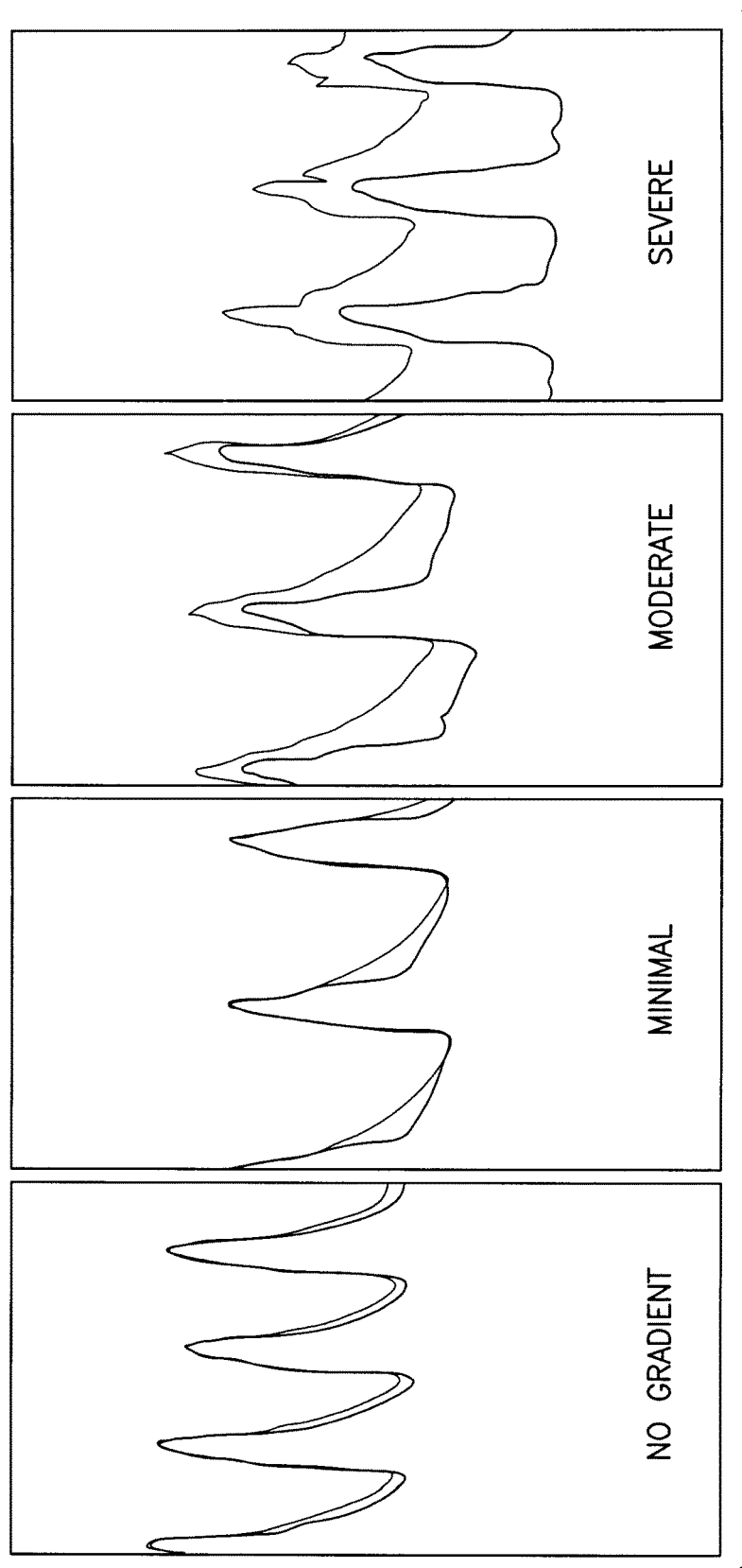
FIG. 1 is a graphical view showing waveform patterns of minimal to severe stenosis in a blood vessel.

In cases where differential viscosity fluids are used with lesser flow rates, the viscosity differences produce an image with standard pressure waveforms similar to hemodynamic signals. Such waveforms are familiar to clinicians who routinely observe pressure waveforms on a hemodynamic monitor during cardiac procedures. Typical waveform patterns showing minimal to severe stenosis are shown in FIG. 1. Pressure differences are still be magnified at the lesion site due to the increased blood viscosity differences alone. Various fluid mechanics formulas may be used to determine pressure drop in a conduit, such as a blood vessel. One such equation is Darcy-Weishbach: $\Delta P = f \times L/D \times ((\rho \times V \times D)/2)$; where: $\Delta P$=pressure drop; f=friction factor; L=artery restriction length; D=average diameter of restricted artery; $\rho$=density of fluid; V=velocity of fluid. Another such equation is: $Q = A \times V$; where: Q=flow rate; A=cross-sectional area of restriction; V=velocity of fluid. A third equation for use in determining pressure drop in a conduit is: $f = 64/Re$; where: f=friction factor and Re=Reynolds number. A fourth equation for use in determining pressure drop in a conduit is: $Re = (\rho \times V \times D)/\mu$; where: Re=Reynolds number; $\rho$=fluid density; V=velocity of fluid; D=diameter of restriction artery; and $\mu$=fluid viscosity.

Accordingly, to increase the measured pressure drop during FFR without using pharmaceuticals, the following discussed relationships may be determined. First, the measured pressure drop across the blood vessel restriction increases as the flow rate increases across the restriction. As noted previously, current practice is to use a vasodilator pharmaceutical to increase blood flow rate. The present method increases flow across the restriction using a steady state and controlled injection fluid across the restriction administered by a power injector, thus causing an increased pressure drop or differential without the need for a pharmaceutical. Next, the pressure differential increases across the restriction as the viscosity of the injected fluid across the restriction increases. In current practice, known FFR measurement techniques typically use the patient's blood. In the present method, the power injector may use a more viscous media such as contrast. Third, the use of a power injector enables the measured pressure drop across a restricted artery to be more accurately correlated to a percentage restriction of the blood vessel (e.g., an artery) without using pharmaceuticals. A suitable power injector for the foregoing application includes an Avanta™ Fluid Management Injection System manufactured by Medrad®, Inc., and disclosed in U.S. Pat. Nos. 7,549,977 and 7,563,249, incorporated herein by reference for details relating to power injectors suitable for the present method.

In one embodiment, an FFR measurement feature may be integrated with an Avanta™ Fluid Management Injection System. In this embodiment, two (2) measurement techniques may be supported with the Avanta™ power injector. This pressure measurement technique involves incorporating an FFR software mode in the Avanta™ Fluid Management Injection System. In this measurement technique, no physical changes to the disposable and hardware portions of the Avanta™ Fluid Management Injection System are required, and the only changes needed are software modifications to the software control system. A second measurement technique involves simultaneous pressure measurements of an occlusion in a blood vessel. This technique allows for two sensing elements to quantify the effect of an occlusion on blood flow in a single measurement.

Figure 2:
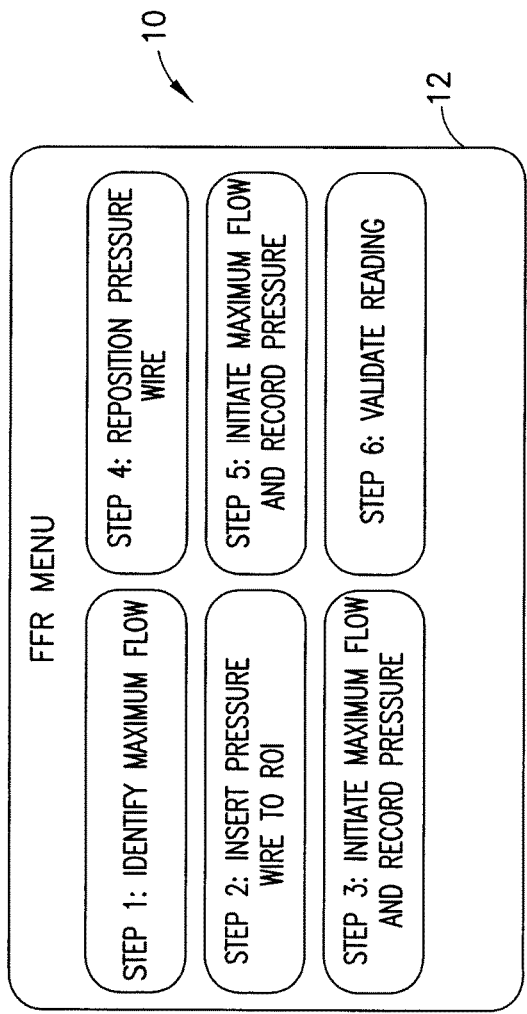
FIG. 2 is a view of a user interface display for a power injector showing an exemplary FFR menu.
Figure 3:
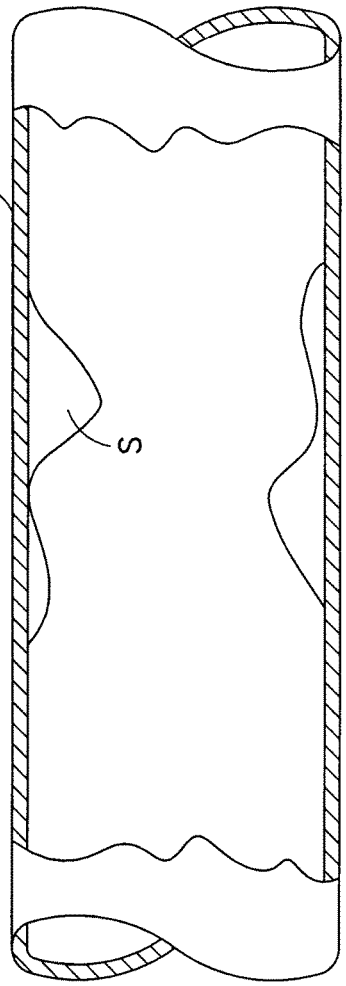
FIG. 3 is a schematic view of a blood vessel with a stenosis.

Referring to FIGS. 2-15, an FFR measurement system 10 is depicted situated in a blood vessel V, such as an artery. This system 10 uses the current physical platform of an Avanta™ power fluid injector 2 with modifications to the software control system of the control unit 4 of the power fluid injector 2, as noted above, which provide a mechanism to inject viscous fluid across an occlusion, lesion, or stenosis S at high flow rates. FFR measuring devices are then be able to quantify stenosis presence S and effect without pacing the heart through a pharmaceutical vasodilator. In FIG. 2, an exemplary Avanta™ user interface screen 12 (e.g., graphical user interface (GUI)) displays the FFR mode, and the user is guided through a series of steps. The user interface screen 12 provides instructions and indicators on how to complete the FFR measurement. Referring to FIGS. 4-5, an initial step in the FFR measurement process is depicted. In this step, the clinician, such as a physician, identifies the maximum contrast flow for the FFR measurement by injecting contrast medium C via a catheter 14 connected to the Avanta™ power fluid injector 2. Initially, the clinician positions the catheter 14 where contrast can be injected under pressure into the direction of blood flow B. The clinician then initiates the contrast injection with a variable hand controller (not shown) associated with the Avanta™ Fluid Management Injection System through the catheter 14. Once retrograde flow R is observed, the maximum flow rate has been achieved. The clinician "saves" this flow rate by pressing, for example, a side (saline) button on the hand controller or by another input to the Avanta™ control system, such as by pressing a button on the user interface screen 12. U.S. Pat. No. 7,313,431 to Uber et al. discloses a methodology for determining retrograde flow R in a blood vessel V, and this patent is incorporated herein by reference for this purpose.

The next step in the FFR measurement process is depicted in FIGS. 6-7. In this step, the clinician places a pressure wire 20 supporting a pressure sensor 22 prior to the beginning of the stenosis S. This wire 20 is introduced using established clinical technique in the same manner as a traditional guide wire. It is desirable to give consideration to ensuring that the contrast medium C does not "jet" across the stenosis S, and side-hole catheters are desirable for this application such as a Vanguard Dx® Angiographic Catheter manufactured by Medrad®, Inc. and disclosed in U.S. Patent Publication No. US 2007/0073271 to Brucker et al., incorporated herein by reference.

Figure 8:
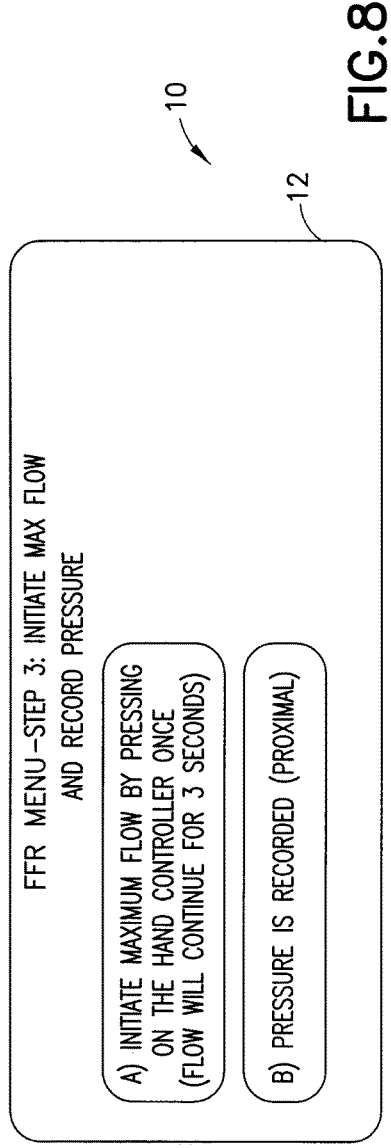
FIG. 8 is a view of the user interface display for a power injector showing an FFR menu and a third step for determining FFR comprising initiating maximum flow rate in the blood vessel of FIG. 3 and recording pressure proximal of the stenosis.
Figure 9:
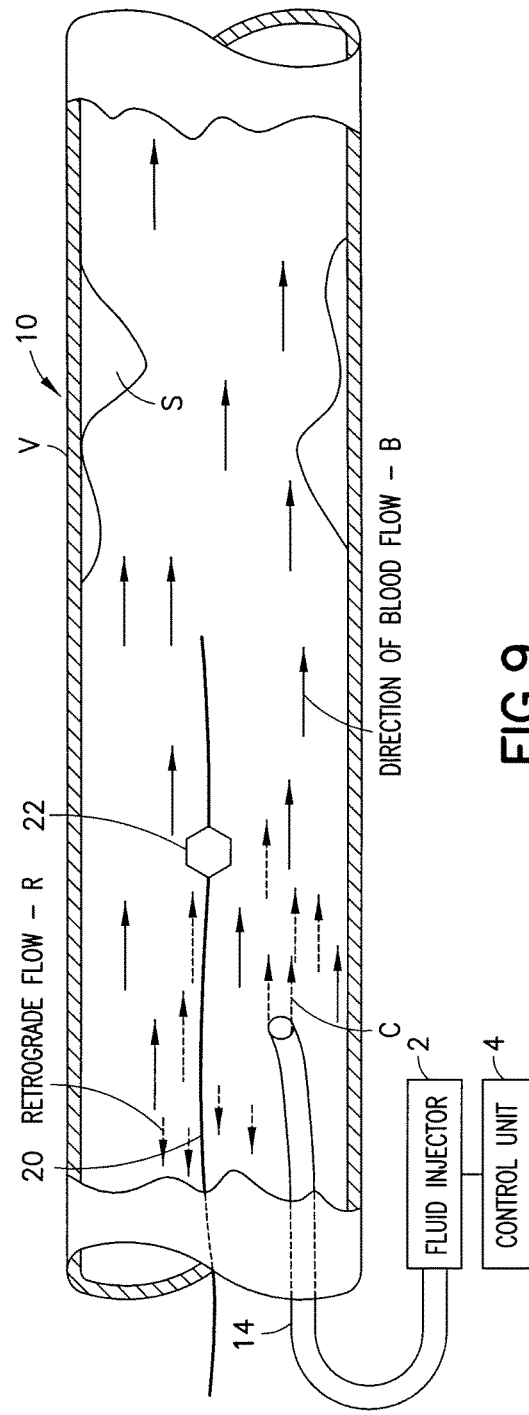
FIG. 9 is a schematic view of the blood vessel with the stenosis of FIG. 3 after initiating maximum flow rate in the blood vessel to record pressure proximal of the stenosis.

Next, the method comprises acquiring a first pressure reading, as depicted by FIGS. 8-9. In this step, the system 10 acquires the first pressure reading via pressure sensor 22 through the support of the Avanta™ power fluid injector 2, and contrast flow C is initiated with the use of the hand controller. In this step of the method, the hand controller acts as a trigger to start a fluid injection in the direction of blood flow B. Once started, the fluid injection continues for three seconds (or other programmed time) at the maximum flow rate determined in the first method step discussed previously. As the fluid injection commences, flow rate and pressure increase in the blood vessel V. This pressure is measured by the pressure sensor 22 (e.g., a pressure transducer) on the pressure wire 20 and is retrieved by the control system of the Avanta™ Fluid Management Injection System. Conditioning logic or other signal filtering techniques in the control system of the Avanta™ Fluid Management Injection System can be employed to prevent a false reading by comparing the output of the pressure sensor 22 before, during, and after the fluid injection. Additionally, sensed conditions are verified to ensure that the pressure sensor 22 does not become lodged into the wall of the blood vessel V. Previous steady state measurements may be employed to ensure the "reasonability" of the returned pressure measurements. Feedback could signal termination of the fluid injection through an Imaging System Interface (ISI) port if the returned signals are not as anticipated. After the fluid injection, pressure normalizes in the blood vessel V and the beginning and ending pressure become the same. Pressure measured during the fluid injection may be filtered for transients along with fluid rise and fall conditions. The proximal pressure measurement is then stored in the Avanta™ control system (e.g., control unit 4) for use in the FFR calculation. While the various FFR measurement techniques described in this disclosure suggest using an existing Avanta™ control system as a suitable control system or device, this should not be deemed exclusive and any logical storage and computation device may also be used for FFR calculations in the various embodiments in this disclosure.

Figure 10:
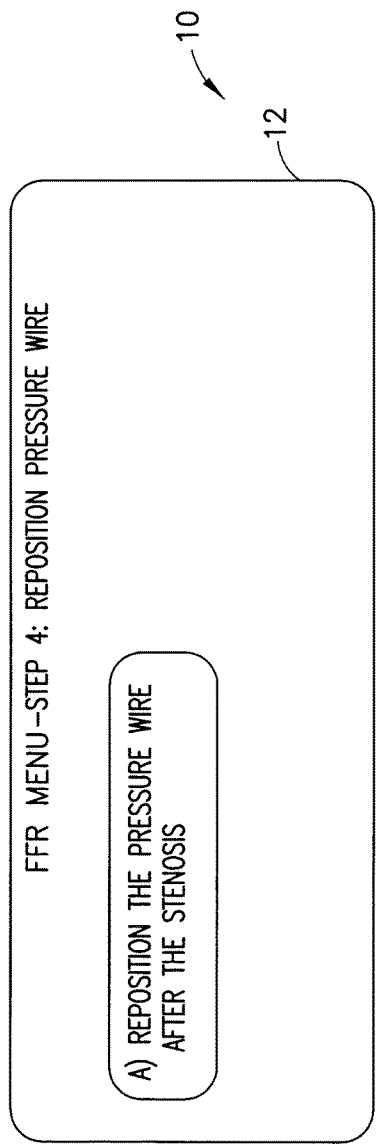
FIG. 10 is a view of the user interface display for a power injector showing an FFR menu and a fourth step for determining FFR comprising repositioning the pressure wire in the blood vessel of FIG. 3.
Figure 11:
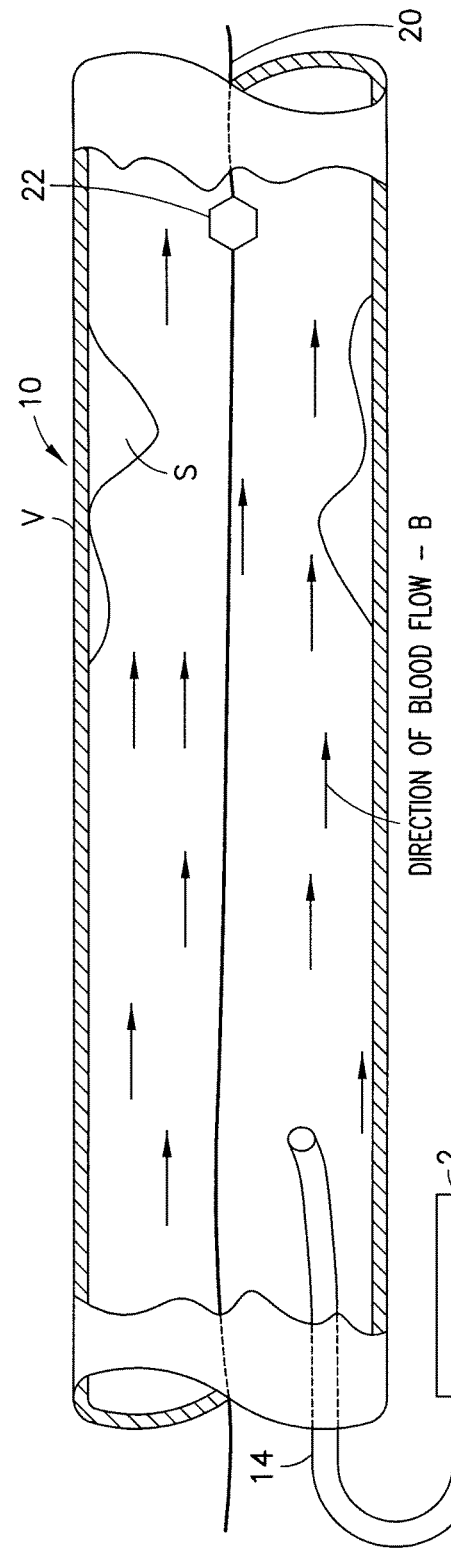
FIG. 11 is a schematic view of the blood vessel with the stenosis of FIG. 3 and showing the repositioned pressure wire in the blood vessel.
Figure 12:
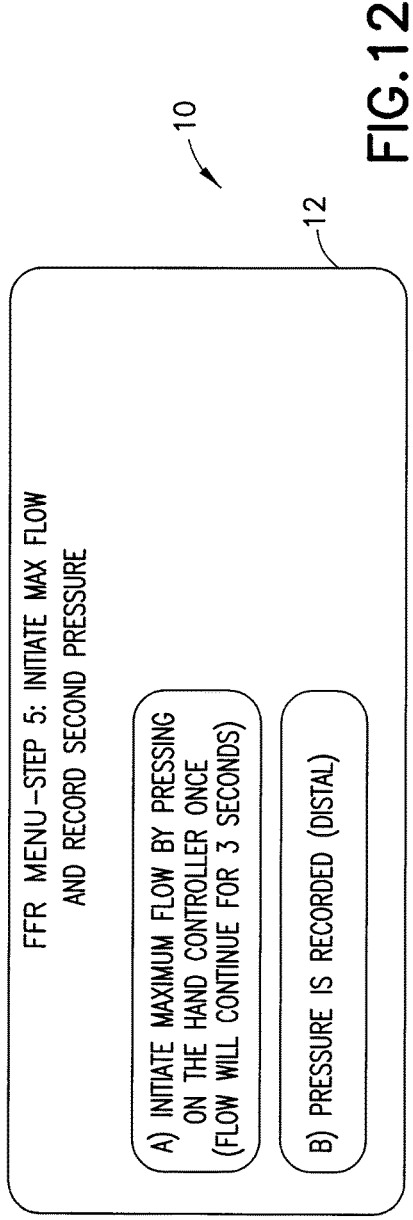
FIG. 12 is a view of the user interface display for a power injector showing an FFR menu and a fifth step for determining FFR comprising initiating maximum flow rate in the blood vessel of FIG. 3 and recording pressure distal of the stenosis.
Figure 13:
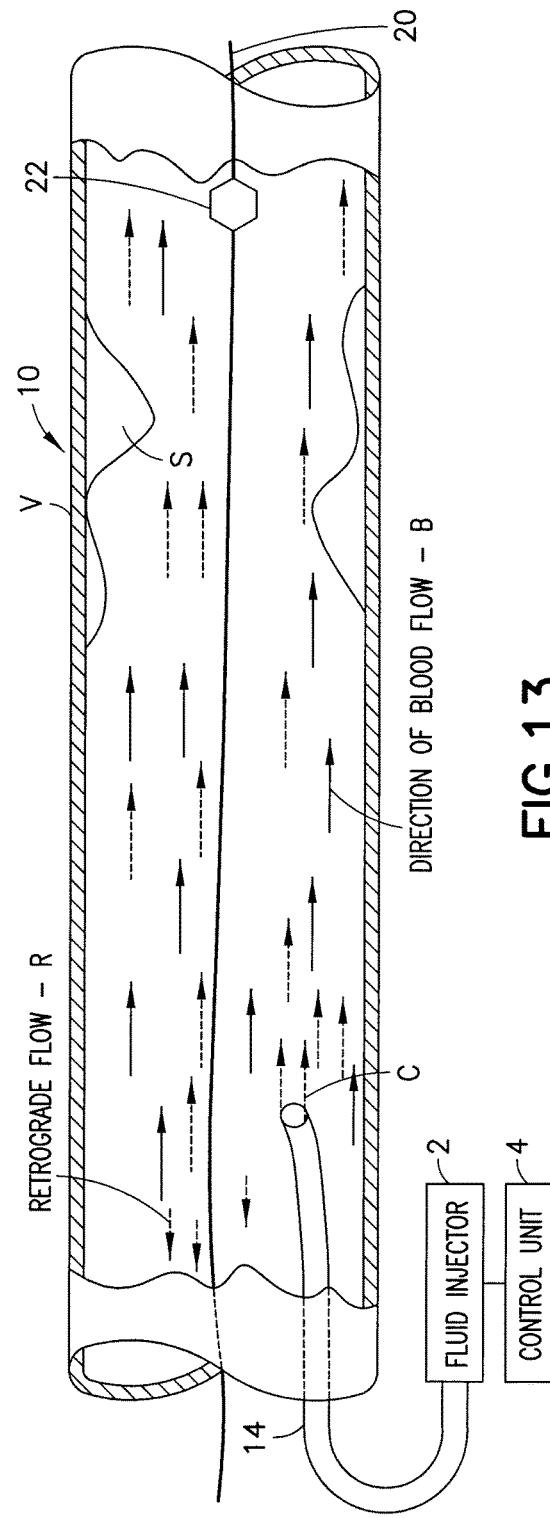
FIG. 13 is a schematic view of the blood vessel with the stenosis of FIG. 3 after initiating maximum flow rate in the blood vessel to record pressure distal of the stenosis.

In a further step in the FFR measurement process, the pressure wire 20 is repositioned in the blood vessel V, as shown in FIGS. 10-11. In this step, the pressure wire 20 is moved distally past the stenosis S to a region behind the occlusion to complete the pressure measurement. The catheter 14 remains in place for the duration of the measurement. Referring further to FIGS. 12-13, the second or distal pressure measurement may now be taken using the pressure sensor 22 on the pressure wire 20. The placement of the pressure sensor 22 past the stenosis S enables the pressure sensor 22 to be exposed to increased flow rates and fluid pressure during a fluid injection. In this case, the hand controller acts as a triggering mechanism to commence the injection of fluid, contrast media C, in the direction of blood flow B. The fluid is injected for three seconds (or other programmed time) while the second measurement is made. During the fluid injection, flow rate and pressure increase in the blood vessel V. This pressure increase is measured by the pressure sensor 22 and is retrieved by the control system of the Avanta™ Fluid Management Injection System. Conditioning logic through signal filtering may be employed to prevent a false reading by comparing the output of the pressure sensor 22 before, during, and after the fluid injection. Additionally, sensed conditions are verified to ensure the pressure sensor 22 does not become lodged into the wall of the blood vessel V. Previous steady state measurements may be used to ensure the "reasonability" of the returned pressure measurements. After the fluid injection, pressure normalizes in the blood vessel V, and the beginning and ending pressure become the same. The pressure measured during the fluid injection is filtered for transients along with fluid rise and fall conditions. The second or distal pressure reading is then stored in the control system of the Avanta™ Fluid Management Injection System for a later calculation. The foregoing fluid injections in the blood vessel V may be accomplished via injection of a contrast medium which may be diluted as desired by saline, as described in U.S. Patent Application Publication No. 2010/0114040 to Schriver et al., which discloses a mixing hand controller of the Avanta™ Fluid Management Injection System.

Figure 14:
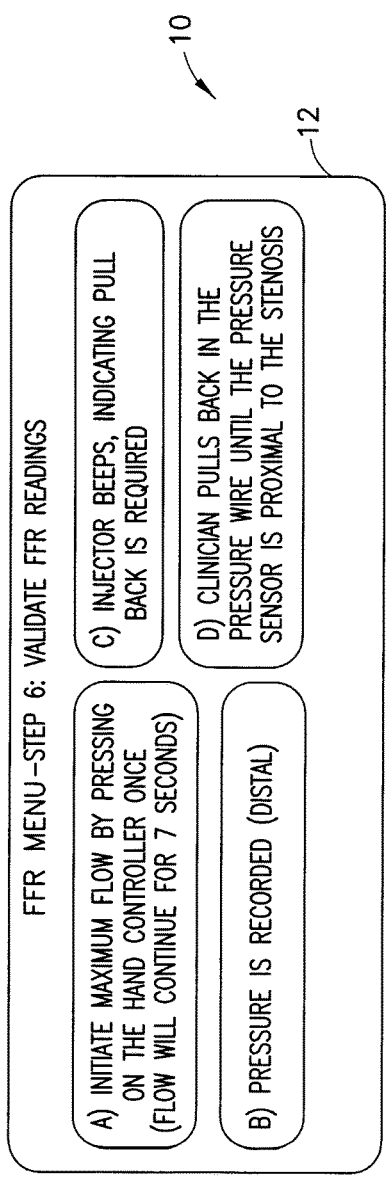
FIG. 14 is a view of the user interface display for a power injector showing an FFR menu and a sixth step for determining FFR comprising validating the FFR pressure reading.
Figure 15:
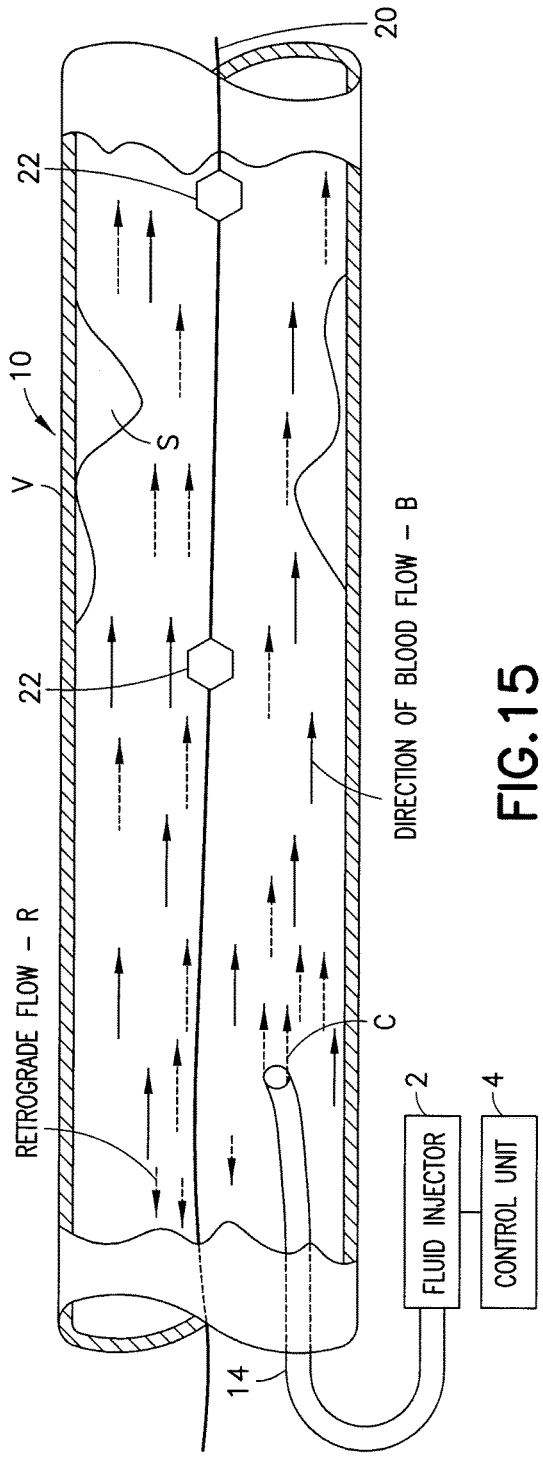
FIG. 15 is a schematic view of the blood vessel with the stenosis of FIG. 3 after initiating maximum flow rate in the blood vessel and subsequent validation of the pressure readings.

FIGS. 14-15 show the validation or confirmation of the FFR measurement. As FIGS. 14-15 reveal, the FFR measurement can be validated in one event. As shown in FIGS. 14-15, the pressure sensor 22 starts at the distal end of the stenosis, or a first ($1^{st}$) position of the pressure sensor 22 shown in FIG. 15. The hand controller acts as an injection trigger for a third and final time. The fluid injection is initiated and the control system of the Avanta™ Fluid Management Injection System indicates that the first measurement is being taken through an audible or visual indication or a combination thereof. After an additional two seconds (or other programmed time), the Avanta™ power fluid injector 2 alerts the clinician by indicating to the clinician to pull back on the pressure wire 20. The clinician pulls back to a location that is proximal to the stenosis S, or to a second ($2^{nd}$) position of the pressure sensor 22 shown in FIG. 15. Throughout this process, pressure measurements are taken using the pressure sensor 22. It can be anticipated that the maximum pressure is proximal to the stenosis S and the minimum pressure is distal to the stenosis S. Time duration of the validation process can vary. Additionally, these pressure measurements could also end with another initiation of the hand controller. FFR is then calculated by Pd/Pp, and both the distal and proximal pressure measurements are filtered MAP (Mean Arterial Pressure) for effect. The FFR value is calculated as a part of the foregoing described methodologies are the same, and differing values could indicate inaccurate technique. Both values are displayed to the clinician for reporting purposes. A quality metric may also provide the clinician with an indication that their measurements are consistent. The FFR values may be stored and recalled as required. In some instances when intervention is required, the first set of FFR values may be compared with a second set after the intervention. This comparison provides a before and after look at flow rate.

In a variation of the foregoing method, simultaneous pressure measurements may be taken, as illustrated in FIGS. 16-23. The simultaneous pressure measurement embodiment of the FFR measurement system 10a is depicted in FIGS. 16-23. This system 10a also uses Avanta™ Fluid Management Injection System with appropriate modification to the control system and disposable set, and a power fluid injector 2a and control unit 4a therefor is shown schematically in these figures. A modified multi-lumen catheter 40 comprising a first fluid conducting/injecting port or lumen 42 and a second hemodynamic monitoring port or lumen 44 may be used in the system 10a, and connected to the power fluid injector 2a. As with the foregoing embodiment of the FFR measurement system 10, the Avanta™ Fluid Management Injection System includes an FFR mode. The FFR mode may be visually distinguishable from the normal operating mode based on bordering and other coloring effects on the user interface display 12a, and provides the clinician with the ability to achieve and identify a maximum flow rate for FFR measurement. Additionally, the FFR mode instructs the clinician on how to operate the device to capture the greatest pressure difference in the presence of maximum flow rate.

Figure 16:
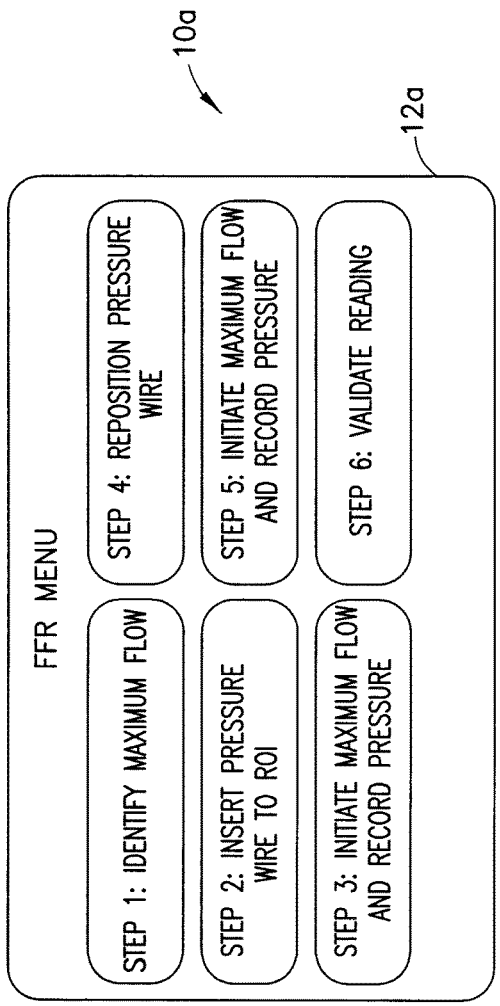
FIG. 16 is a view of a user interface display for a power injector showing an alternative embodiment of an exemplary FFR menu.
Figure 17:
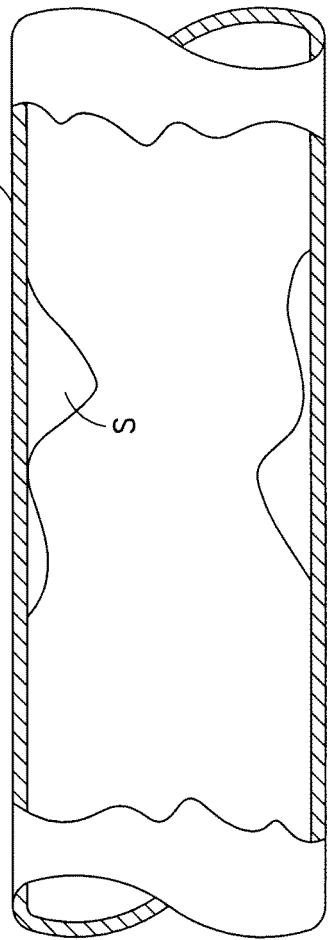
FIG. 17 is a schematic view of a blood vessel with a stenosis.

In FIG. 16, an exemplary user interface display 12a for the Avanta™ Fluid Management Injection System is shown displaying the FFR mode. In FIG. 17, the blood vessel V is shown with a stenosis S in a similar manner to FIG. 3. The user interface display 12a is used to guide the user through a series of operational steps, and the user interface display 12a provides instructions and indicators on how to complete the required measurements. Referring to FIGS. 18-19, the clinician first identifies the maximum contrast flow for the FFR measurement. In this method step, the clinician positions the catheter 40 to a position where the catheter 40 can inject contrast medium C under pressure via the fluid injecting lumen 42 using the power fluid injector 2a. The clinician then initiates the contrast medium C injection with the variable hand controller from the Avanta™ Fluid Management Injection System. Once retrograde flow R is observed, the maximum flow rate has been achieved and the clinician "saves" this flow rate by pressing on the side (saline) button on the hand controller or by another input to the control system such as by pressing a button on the user interface display 12a.

Figure 20:
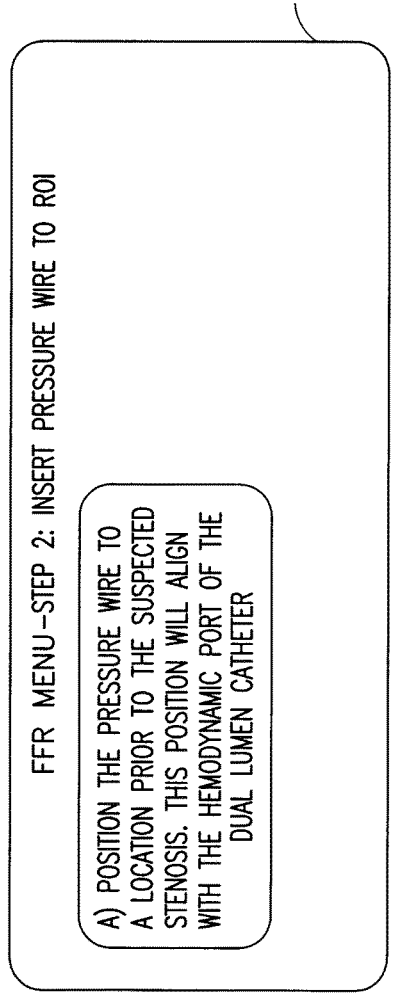
FIG. 20 is a view of the user interface display for a power injector showing an FFR menu comprising inserting a pressure wire into the blood vessel of FIG. 17.
Figure 21:
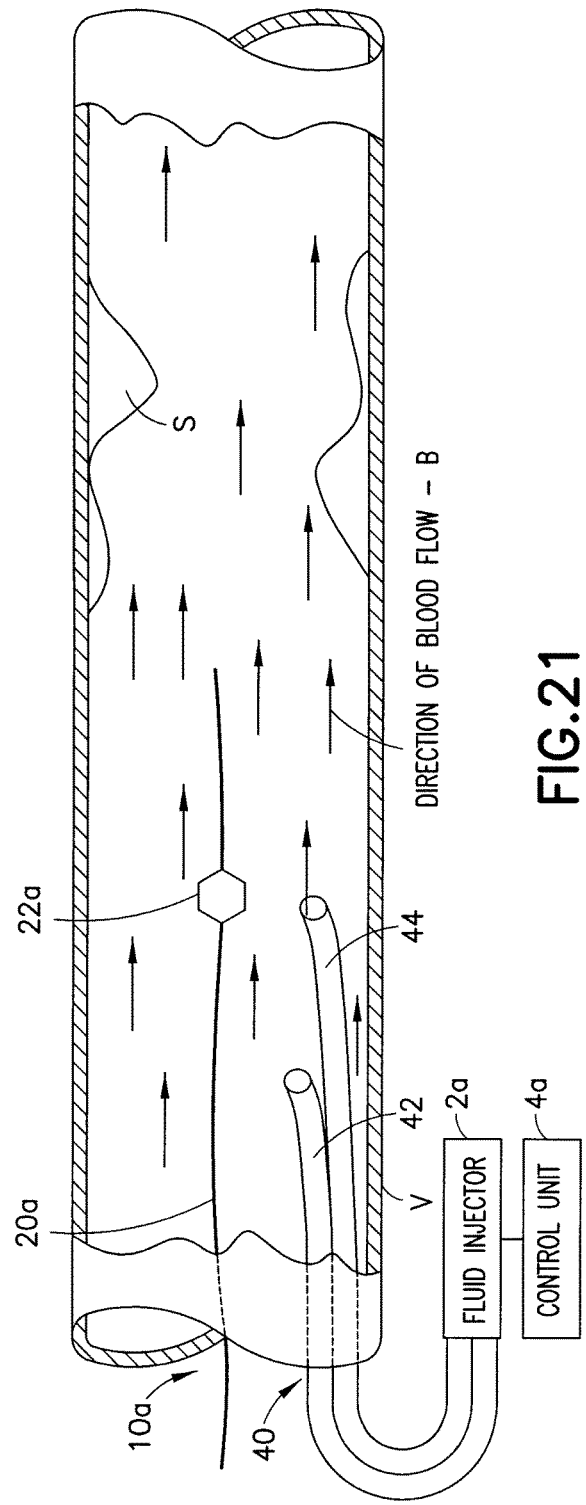
FIG. 21 is a schematic view of the blood vessel with the stenosis of FIG. 17 and showing a pressure wire inserted into the blood vessel.

Referring next to FIGS. 20-21, the next FFR measurement method step is illustrated. In FIGS. 20-21, the clinician places the pressure wire 20a just prior to the beginning of the stenosis S. The pressure wire 20a supporting one or more pressure sensors 22a may be introduced using established clinical technique in the same manner as a traditional guide wire. Again, consideration can be given to ensuring that the contrast medium C does not "jet" across the across the stenosis S, and side-hole catheters are desirable for this application, as indicated previously. Ideally, the hemodynamic monitoring port or lumen 44 aligns with the pressure wire 20a, so that both a hemodynamic monitoring port or lumen 44 and the pressure sensor 22a read the same hemodynamic signal.

Figure 22:
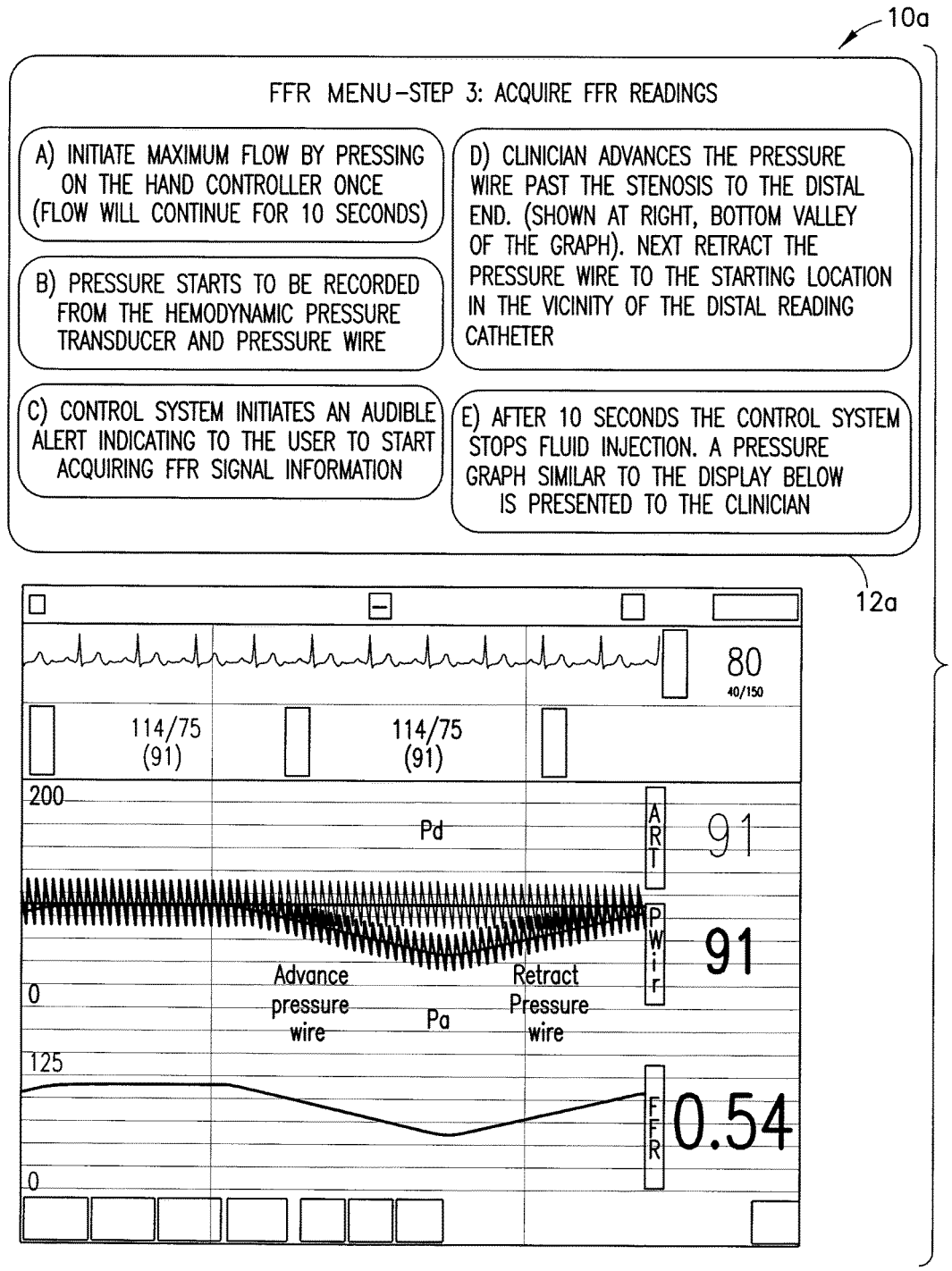
FIG. 22 is a view of the user interface display for a power injector showing an FFR menu comprising acquiring proximal and distal pressure readings across the stenosis.
Figure 23:
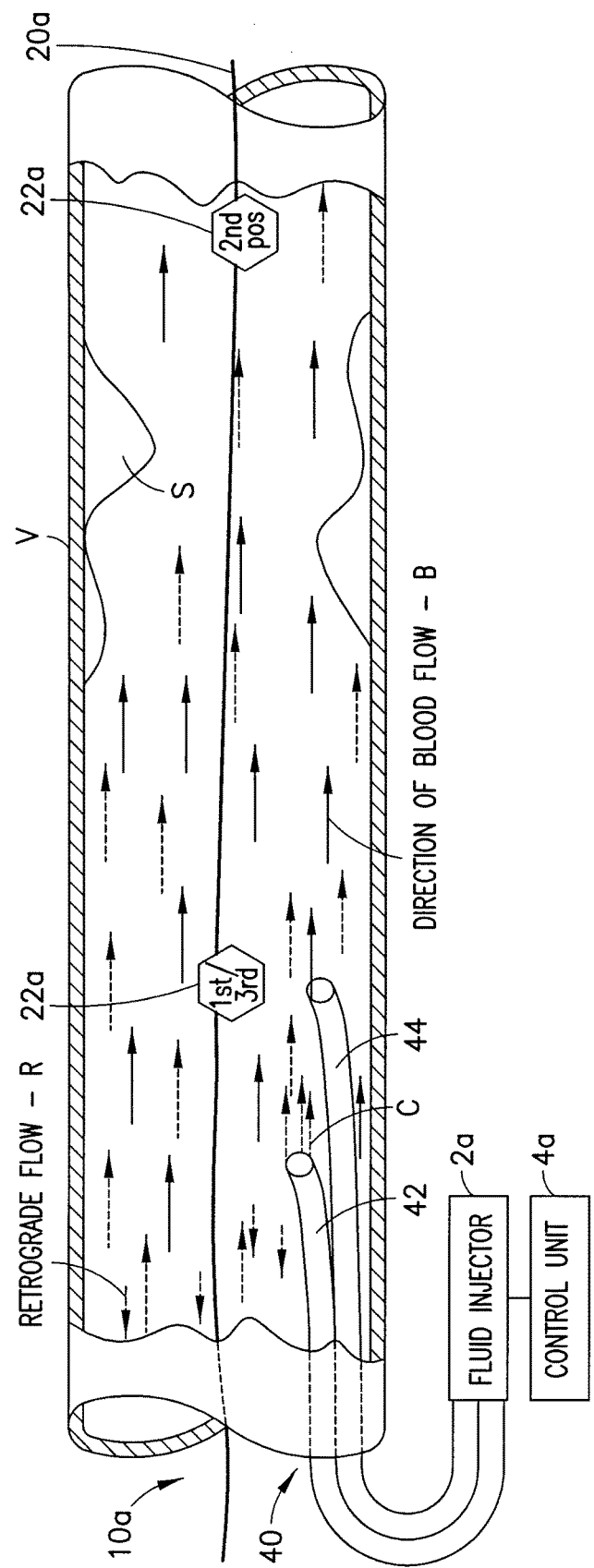
FIG. 23 is a schematic view of the blood vessel with the stenosis of FIG. 17 to acquire the proximal and distal pressure readings across the stenosis.

FIGS. 22-23 next depict the acquisition of the first pressure measurement reading. In this step, the FFR measurement system 10a is shown to acquire the first pressure reading through the support of the Avanta™ power fluid injector 2a. Contrast medium C flow is initiated with the use of the hand controller from the Avanta™ Fluid Management Injection System, which actuates the power fluid injector 2a to inject contrast medium C. In this step of the process, the hand controller acts as a trigger to start a fluid injection using the Avanta™ power fluid injector 2a and contrast medium C in injected via the fluid injecting port or lumen 42 of the catheter 40. Once started, the fluid injection continues for ten seconds (or other programmed amount) at the maximum flow rate determined previously. Pressure readings proximal or distal of the stenosis S are taken substantially simultaneously using the pressure sensor 22a and the hemodynamic monitoring port or lumen 44 on the catheter 40.

The Avanta™ control system typically initiates an audible and/or visual alert indicating to the user to start acquiring an FFR signal. Flow rate and pressure increase in the blood vessel V as fluid is injected by the Avanta™ power fluid injector 2a and contrast medium C in injected via the fluid injecting port or lumen 42 of the catheter 40. The fluid pressure is measured by the hemodynamic monitoring port or lumen 44 of the catheter 40 and by the pressure sensor 22a at the first ($1^{st}$) position shown in FIG. 23. Both readings are recorded by the Avanta™ control system. Once the clinician is alerted, the pressure wire 20a is advanced past the stenosis S to the distal end thereof, where the pressure sensor 22a is placed at a second ($2^{nd}$) position as shown in FIG. 23. Fluid, such as contrast medium C, is again injected into the blood vessel V using the power fluid injector 2a via the fluid injecting port or lumen 42 of the catheter 40 for a preset period of time, such as 3 seconds, and until retrograde flow R is again observed in the blood vessel V. Pressure readings may be taken substantially simultaneously distal of the stenosis S using the pressure sensor 22a and proximal of the stenosis S using the hemodynamic monitoring port or lumen 44 on the catheter 40.

Next, the clinician retracts the pressure wire 20a to its starting location, where the pressure sensor 22a is placed at a third ($3^{rd}$) position as shown in FIG. 23, and fluid, such as contrast medium C, is again injected into the blood vessel V using the power fluid injector 2a via the fluid injecting port or lumen 42 of the catheter 40 for a preset period of time, such as 3 seconds, and until retrograde flow R is again observed in the blood vessel V. This last position is in the vicinity of the hemodynamic monitoring port or lumen 44 of the catheter 40 and pressure readings may again be taken simultaneously using the pressure sensor 22a and the hemodynamic monitoring port or lumen 44 of the catheter 40. Physicians/clinicians often use this last step to validate that the pressure readings before the stenosis S are read identically by both sensors. If for any reason the pressure readings are different, the physician or clinician may recalibrate and measure again.

Conditioning logic through signal filtering embedded as part of the Avanta™ control system prevents a false reading by comparing the output of the pressure transducer 22a before, during, and after the fluid injection. Additionally, sensed conditions are verified to ensure that the pressure transducer 22a does not become lodged into the wall of the blood vessel V. Previous steady state measurements may be used ensure the "reasonability" of the returned pressure measurements. After the fluid injection, pressure normalizes in the blood vessel V and the beginning and ending pressure become the same. Pressure measured during the fluid injection may be filtered for transients along with fluid rise and fall conditions. The pressure is then stored for use in the FFR calculation. FFR is then calculated by Pd/Pp and both the distal and proximal pressures may be filtered for effect. FFR values may be stored and recalled as required. In instances when intervention is required, the first set of FFR values may be compared with a second set. This provides a before and after look at flow rate as provided by FFR measurement.

Figure 24:
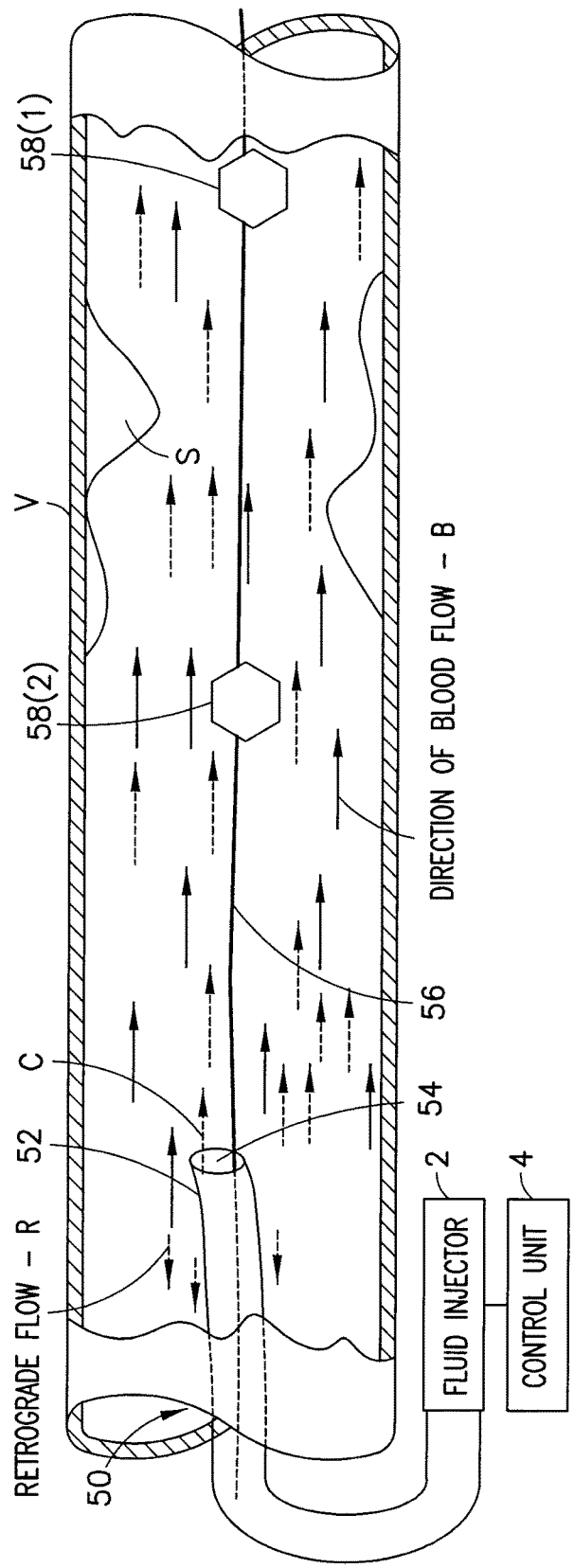
FIG. 24 is a schematic view of the blood vessel with the stenosis of FIG. 17 showing an alternative of a pressure sensing arrangement for acquiring simultaneous proximal and distal pressure readings across the stenosis.

A variation of the foregoing simultaneous measurement methodology is illustrated in FIG. 24. In this alternate method of simultaneous pressure measurement, a catheter 50 may be provided having a distal end 52 defining a distal end opening 54 that allows for a dual pressure sensing wire 56 to extend past the distal end opening 54. The dual pressure sensing wire 56 comprises two pressure sensors 58(1), 58(2) axially spaced apart on the dual pressure sensing wire 56 so as to extend past the distal end opening 54. In this embodiment, side holes (not shown) on the catheter 50 diffuse fluid medium, contrast medium, while the distal end 52 allows for exact placement of the dual sensing pressure wire 56. This embodiment of the catheter 50 eliminates the need for the clinician to reposition the catheter 50 once it is placed and only the dual pressure sensing wire 56 needs positioning. The Avanta™ power fluid injector 2 and control system or unit 4 may be used in the embodiment shown in FIG. 24.

Figure 25:
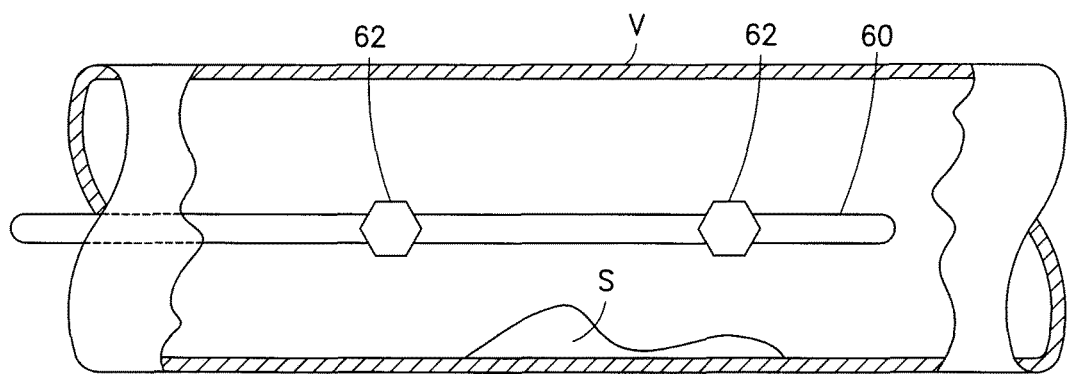
FIG. 25 is a schematic view of the blood vessel with the stenosis of FIG. 3 or FIG. 17 showing a guide wire supporting optical sensors.
Figure 26:
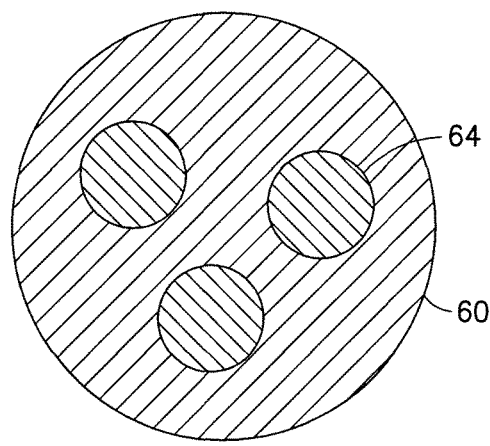
FIG. 26 is a schematic cross-sectional view of the guide wire of FIG. 25.

In another embodiment, as shown in FIGS. 25-26, a guide wire 60 may comprise numerous sensors 62. The guide wire 60 may define an internal cavity and have an optical shielding covering that protect against X-rays. Certain known guide wires and/or catheters currently provide a damped way to view hemodynamic signals. However, these known devices can also act as a medium for carrying optical wires used for transmitting pressure data. These known guide wires have internal cavities initially designed to act in many of the same ways as a traditional catheter. Depending on the internal diameter (ID) of a guide wire, numerous optical wires can be placed. In the guide wire 60 shown in FIG. 25, a metal based covering, such as Nitenol, may be used to enhance protection for internal optical wires 64 to guard against light and/or X-Ray emissions. Holes or cutouts may also be provided to enable the optical sensors 62 to protrude from the guide wire 60 and/or a catheter. This feature enables the external facing portion of the sensor 62 to exit the guide wire 60 and/or catheter while the internal portions remain protected. Thus, only the sensing portions of the sensors 62 interact with the pressure produced by blood flow in blood vessel V. Fluoroscopic markers may also be placed on the guide wire 60 and/or catheter to facilitate placing a portion of the guide wire 60 proximal to the stenosis S and to ensure that an optical sensor 62 is placed distal of the stenosis S. This placement enables the measurement of the lesion without continual retries or sensor repositioning. The optical wires 64 provide additional material in the guide wire 60 and/or catheter to permit greater torque to be applied to the guide wire 60 and/or catheter when placing the assembly in the blood vessel V. The guide wire 60 with optical sensors 62 may be used with traditional FFR measurement techniques such as increasing cardiac output through a vasodilator, and may also be used in any of the FFR measurement techniques described in the foregoing.

Figure 27:
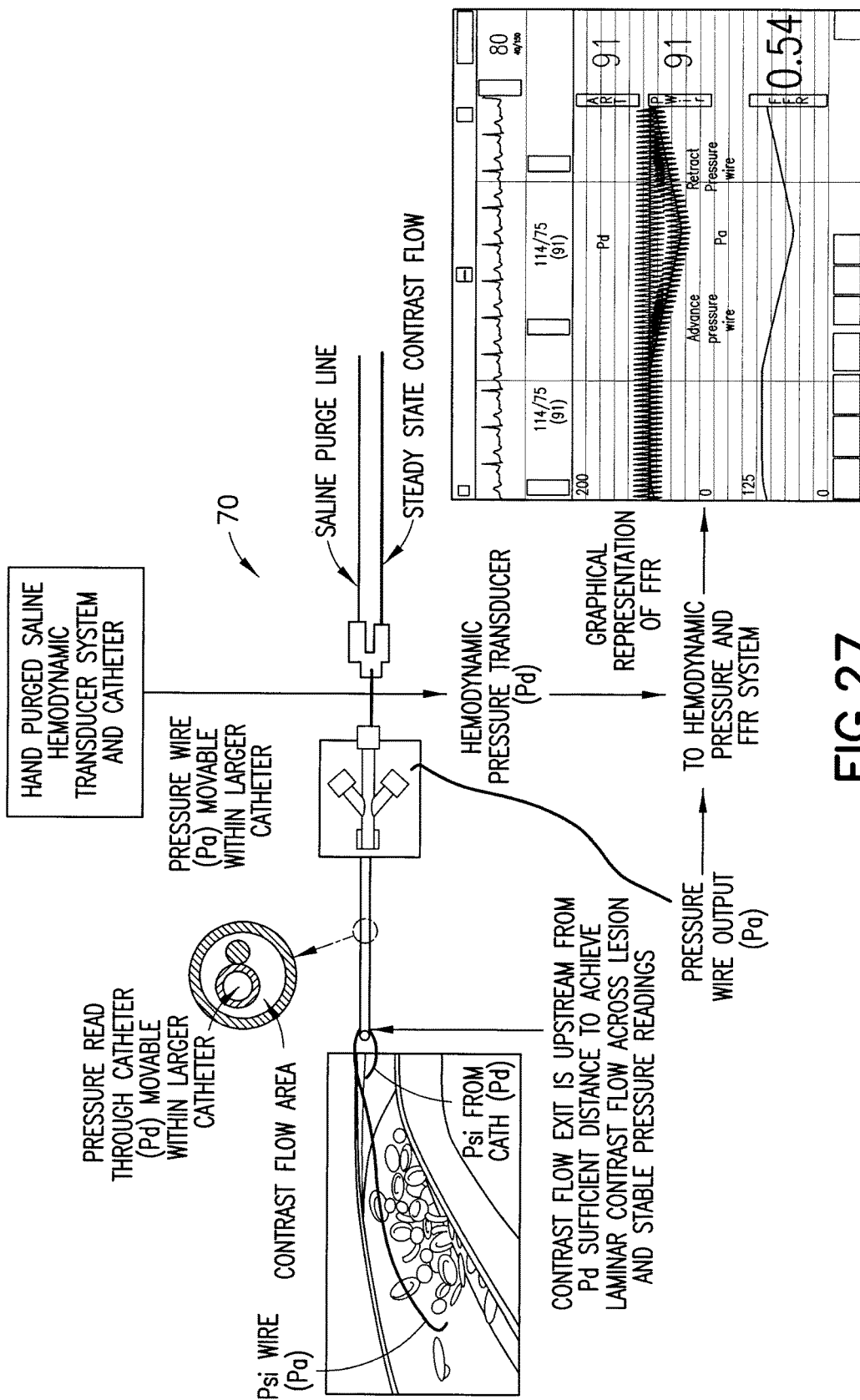
FIG. 27 is a schematic view of a fluid path set for use with a power injector to determine FFR in a blood vessel.

Referring next to FIG. 27, an FFR measuring catheter 70 for suitable application in connection with the Avanta™ Fluid Management Injection System is disclosed in U.S. Pat. Nos. 7,549,977 and 7,563,249, incorporated herein by reference previously.

In a further embodiment, a carrier 100 may be provided to support multiple optical sensors and is shown in FIGS. 28-31. The carrier 100 may include a variety of intra-arterial and venous devices or fluid that enter the vasculature and help to identify and/or treat disease. By adding pressure sensing capability to these devices, longer term measurement of performance characteristics through pressure drop measurements may be accomplished. The carrier 100 may be in the form of, for example: permanent and semi-permanent stents; umbrella filters; temporary implantable support rings for sensors, catheters of various sizes, magnetically and other steerable devices, and fluid sail devices, as a set of non-limiting examples.

In FIG. 28, a carrier 100 in the form of an implantable support ring carrier 102 is shown. The support ring carrier 102 is used to support pressure sensors 104 on a bioabsorbable magnesium material or similar material that will degrade over time. As identified in medical literature (see The Lancet, Volume 369, Issue 9576, incorporated here in by reference), this kind of material may be used to provide infrastructure scaffolding to support the pressure sensors 104. In the present application, the pressure sensors 104 could be mounted on the degradable material and then placed in regions where FFR measurement aid in the detection and quantification of stenosis S. The pressure sensors 104 may also remain in such positions until any interventional procedures are complete.

In FIG. 29, the carrier 100, as illustrated in the embodiment shown in FIG. 28, is combined with a stent 110. Using this arrangement, a clinician may leave the measurement capability in place for a variety of time frames that are dependent on prescribed treatment options. For example, the carrier 100 may be left for a period of minutes until the stent 110 is placed. Dilution solutions enable the supporting bioabsorbable material to degrade and the pressure sensors may be removed 104. Additionally, the pressure sensors 104 may be left in the patient for an extended period of time in order to monitor the effects of thrombus on a particular region of interest. For example 30, 60, 90 days of monitoring can provide enhanced knowledge of stent restenosis. This long term placement is especially useful in patients who do not have conforming anatomy and are susceptible to restenosis. The carrier 100 in FIG. 29 may be provided with pressure sensors 104 that may be used as part of a method of monitoring intra-arterial blood pressure in patients over an extended period of time. One or more of the pressure sensors 104 enable constant monitoring of patients with chronic conditions. For example, patients with peripheral thrombus might have sensors mounted distally in the arms or legs and the signal supplied by these pressure sensors 104 may be compared with a signal supplied by another sensor located in the left ventricle. Collectively, these pressure sensors 104 enable a clinician to compare the effects of thrombus over time. Other pertinent applications for the carrier 100 shown in FIG. 29 areas include early stroke warning and vital organ monitoring, as non-limiting examples.

Figure 30:
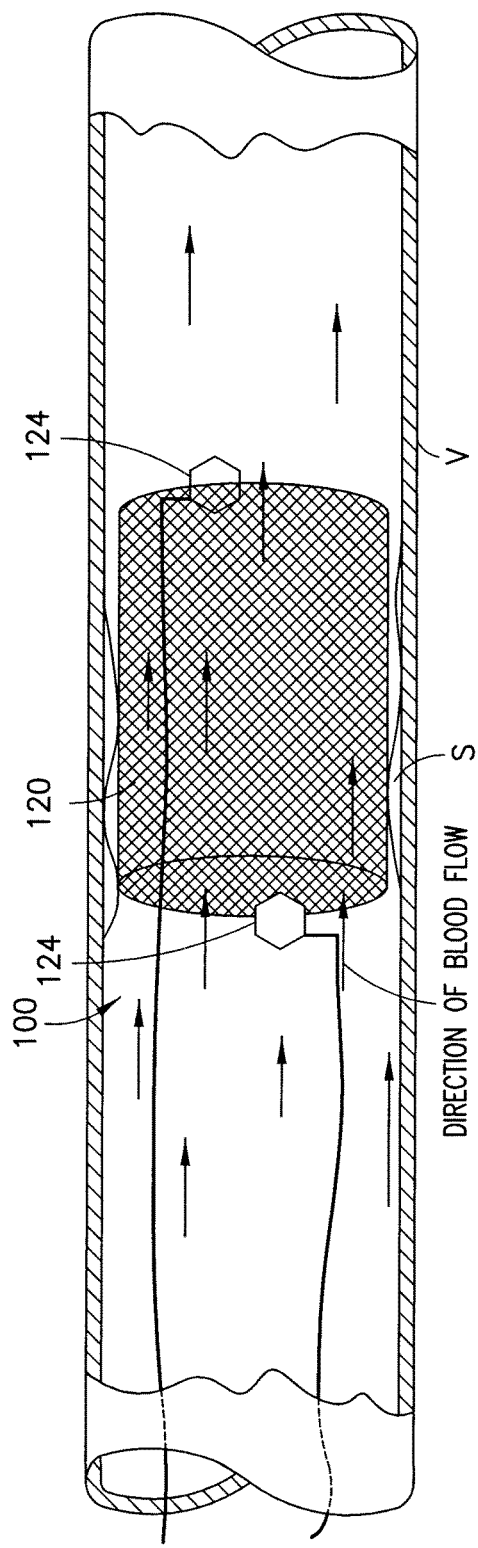
FIG. 30 is a schematic view of a blood vessel with a stenosis and showing an implantable stent for supporting pressure sensors and the like, proximal and distal of the stenosis.

In FIG. 30, the carrier 100 comprises a permanent or semi-permanent stent 120. In a similar manner to the embodiment of the carrier 100 shown in FIG. 29, the stent carrier 120 may comprise pressure sensors 124 that are placed on the deployed stent body. The pressure sensors 124 may be used to provide a real-time knowledge of thrombus and other occlusions. Output or signal lines (not shown) from the pressure sensors 124 may be connected to a transmit-and-receive box located remotely from the stent carrier 120. This box may be configured to be primarily responsible for communicating the effects of blood flow on the stent carrier 120. As the stent carrier 120 becomes occluded over time, a clinician would be able to measure its effective flow capacity.

In addition to the foregoing "ring" carrier 102 (FIG. 29) and stent carrier 120 (FIG. 30), other applications for the stent carrier 100 may include a battery powered device, similar to pacemakers. Additionally, microwave power can provide enough current to sample the pressure sensors 104, 124 and provide readings. Further, vibration technology could also power such a device. In any of these embodiments, follow-up office type appointments enable caretakers to understand the performance of, for example, the stent carrier 120.

Blood flow may or may not be altered during the pressure reading process in the various embodiment of this disclosure. Little or no increase to blood flow is not an ideal measurement, but does provide a mechanism to quantify performance based on relatively normal flow. However, since exercise increases blood flow and enhances accuracy, sampling during a physical activity provides a desirable measurement situation. Pressure readings can occur immediately after installation in the patient's body or over long periods of time. Depending on battery life or external power, pressure readings are available for the life of the stent carrier 120. Any location in the body can provide an opportunity for pressure measurement, and the foregoing "ring" carrier 102 (FIG. 29) and stent carrier 120 (FIG. 30) aid in the internal/external reading of such pressures.

Figure 31:
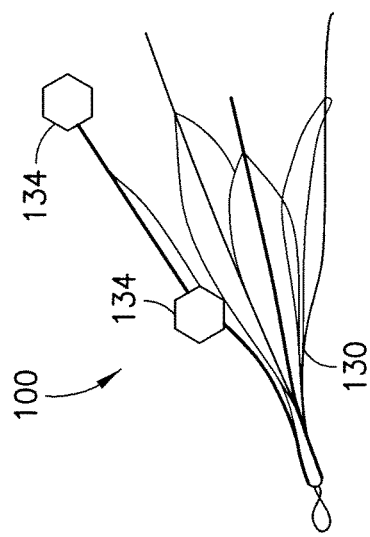
FIG. 31 is a schematic view of an umbrella filter for supporting pressure sensors and the like, proximal and distal of a stenosis.
Figure 32:
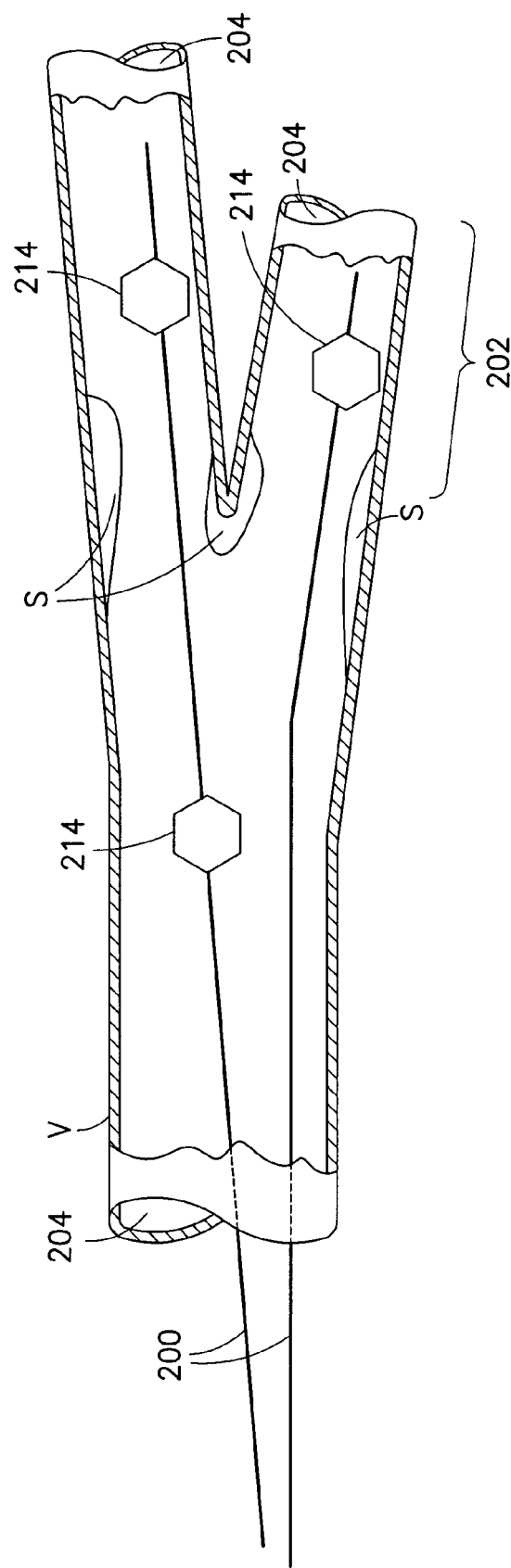
FIG. 32 is a schematic view of a bifurcated blood vessel with a stenosis and showing a multi-pressure wire arrangement for determining pressure proximal and distal of the stenosis.
Figure 33:
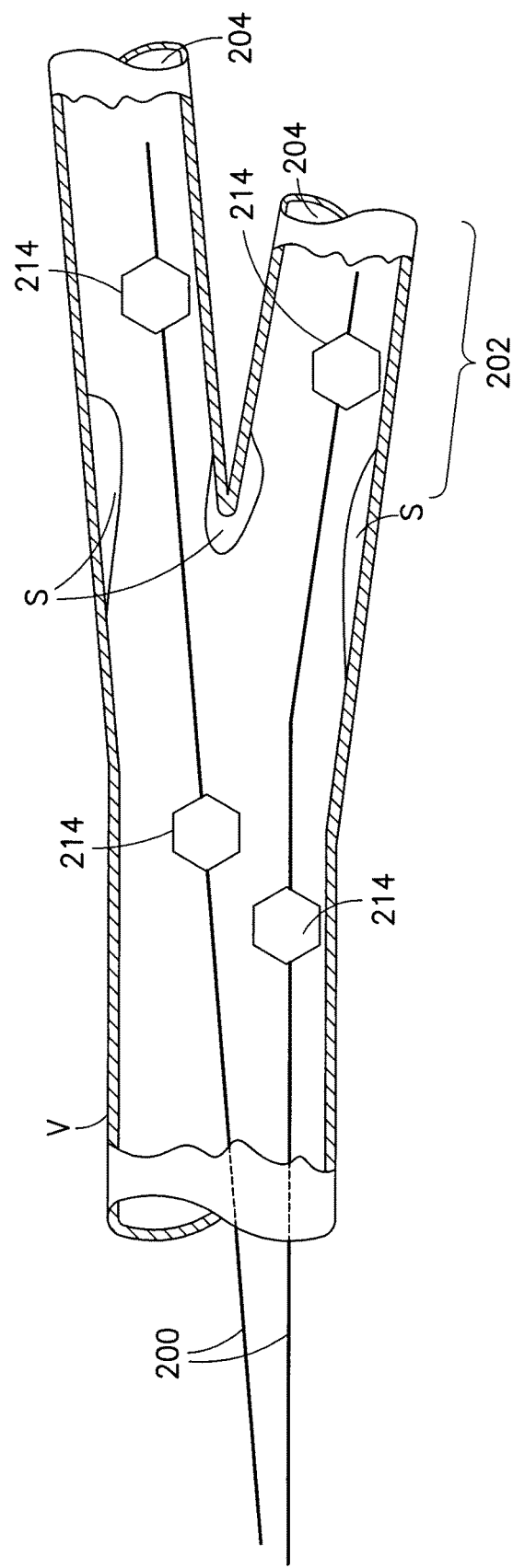
FIG. 33 is a schematic view of a bifurcated blood vessel with the stenosis of FIG. 32 and showing a multi-pressure wire arrangement comprising four optical sensors for determining pressure proximal and distal of the stenosis.
Figure 34:
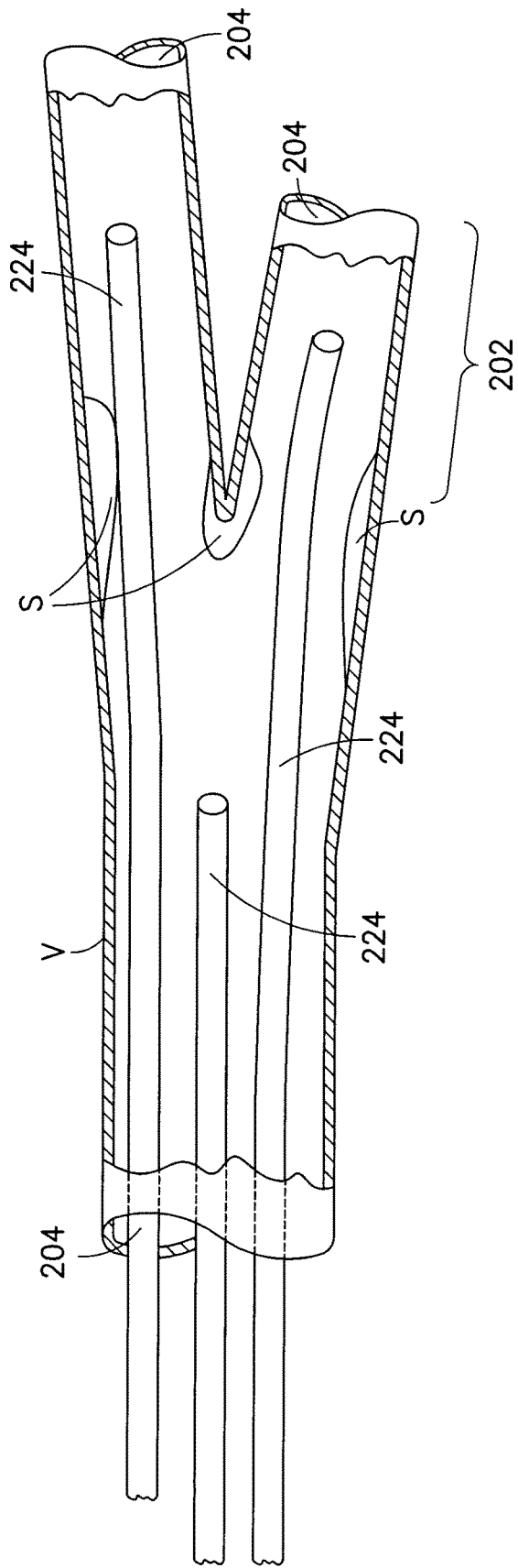
FIG. 34 is a schematic view of a bifurcated blood vessel with the stenosis of FIG. 32 and showing use of three hemodynamic catheters for determining pressure proximal and distal of the stenosis as an alternative to the pressure sensing arrangements shown in FIGS. 32-33.
Figure 35:
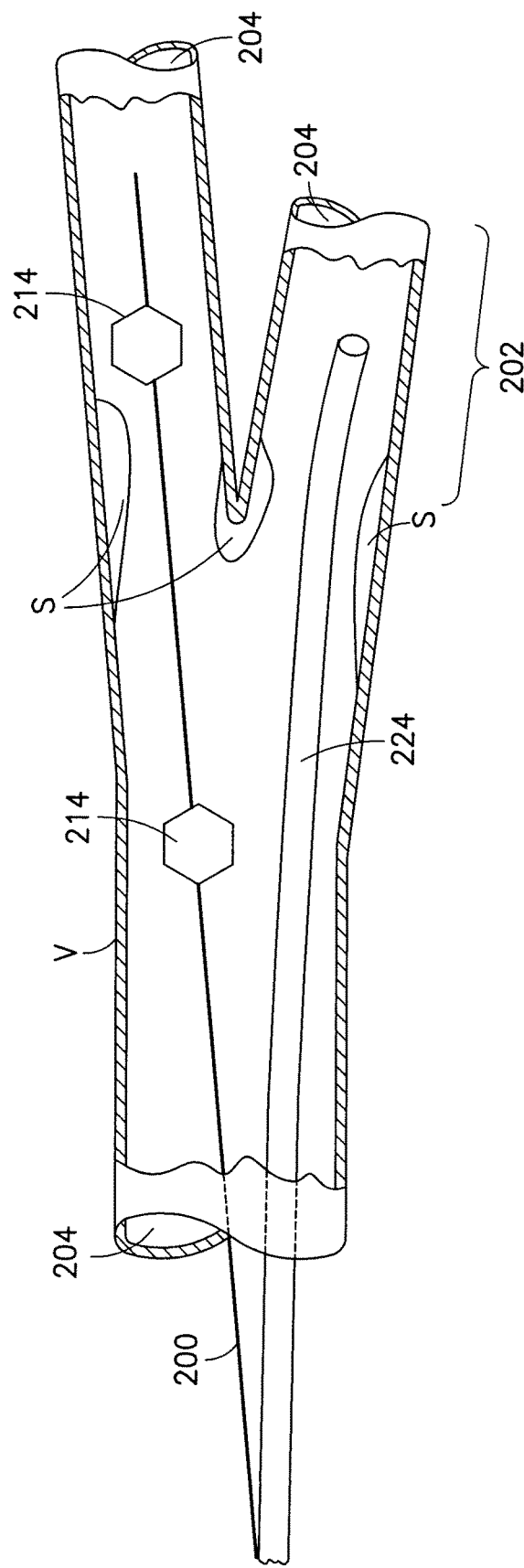
FIG. 35 is a schematic view of a bifurcated blood vessel with a stenosis of FIG. 32 and showing use of a combination of pressure wires and hemodynamic catheters for determining pressure proximal and distal of the stenosis as an alternative to the pressure sensing arrangements shown in FIGS. 32-34.

In FIG. 31, the carrier 100 comprises an umbrella filter carrier 130. Umbrella filters are commonly deployed in the inferior vena cava to prevent strokes like pulmonary embolisms. These devices are often temporary and removed when a patient is no longer at risk for blood clots. Although primarily implemented in the inferior vena cava, an umbrella filter may also be placed in the infra-renal, supra-renal, supra-hepatic, and superior vena cava, among other locations. Multiple pressure sensors 134 can be placed on the umbrella filter carrier 130 to detect blood clots and other occlusions.

Often, coronary occlusions are found at the intersection points of a coronary tree. These intersection points might involve two, three, or more pathways. With reference now to FIGS. 32-35, in another embodiment, multiple pressure wires 200 may be placed down a bifurcation 202 in a blood vessel V having a stenosis S, and each vessel branch 204 receives one or more pressure and/or flow measuring sensors 214. Collectively, the pressure and/or flow measured from these sensors 214 total the cardiac output from the "root" or supplying branch 204. In the cases where a stenosis S is found, the combined pressure drop is indicative of an occlusion. In the present embodiment, three (3) separate occlusions or stenoses S are illustrated in FIGS. 32-35, and each of these occlusions or stenoses S is located in the vicinity of the intersection point or bifurcation 202. These illustrations are exemplary and are intended to depict one, two, three, or more locations where occlusions occur at or around the bifurcation 202. Similar conditions also exist at blood vessel trifurcations. In the pressure sensing arrangement shown in FIG. 32, three (3) pressure sensors 214 are deployed. In the pressure sensing arrangement shown in FIG. 33, four (4) pressure sensors 214 are deployed. In the pressure sensing arrangement shown in FIG. 34, three (3) hemodynamic monitoring catheters 224 are deployed. In the pressure sensing arrangement shown in FIG. 35, two (2) pressure sensors 214 are deployed in one vessel branch 204 and a hemodynamic monitoring catheter 224 is deployed in the second vessel branch 204.

Figure 36:
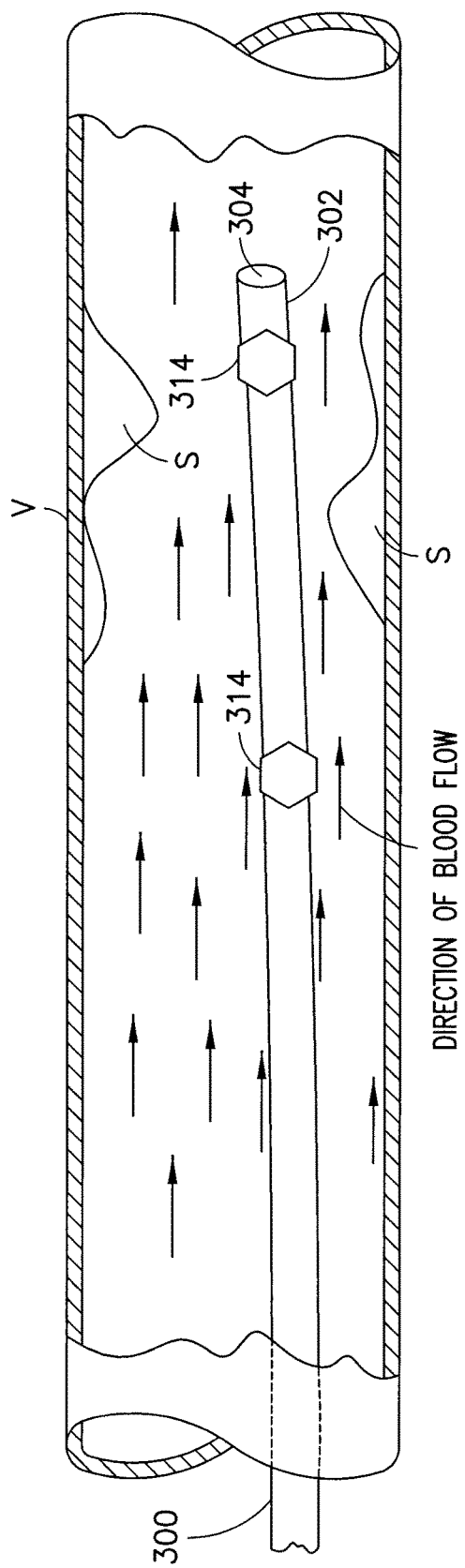
FIG. 36 is a schematic view of a blood vessel with a stenosis showing a thrombus removal catheter comprising pressure sensors for determining pressure proximal and distal of the stenosis as an alternative to the pressure sensing arrangements shown in FIGS. 32-35.

In another embodiment, FFR measurement capability may be provided on a thrombus removal catheter, as shown in FIG. 36, for the purposes of providing feedback to the clinician about the performance of aspiration activity, reducing contrast load and hemolysis, etc. For example, any manual catheters, assisted manual catheters, and mechanical thrombus removal catheters may be used in the embodiment shown in FIG. 36.

In the embodiment shown in FIG. 36, a thrombus removal catheter 300 is shown with several small pressure sensors 314, similar to common fiber optic or miniature MEMs based physiological pressure sensors, are located along the length of a thrombus removal catheter 300. The pressure sensors 314 are typically flush with the exterior wall of the catheter 300. Specifically, two (2) pressure sensors 314 may be located near a distal end 302 of the catheter 300 in the vicinity of the aspiration point or tip 304. The two (2) distal pressure sensors 314 may be separated by a distance that is most appropriate for the size of lesion or thrombus that is common to a particular region. Additional pressure sensors (not shown), such as a third or fourth sensor, may be located several inches from the aspiration opening or tip 304, and these additional sensors can provide details about lengthy thrombus blood clots that have gradual effects on blood flow. Signal wires (not shown) may be embedded through the length of the catheter 300. The catheter 300 may have additional connection points at the proximal end, which can be used to convert optical or MEMs signals to electrical pressure waves. Pressure waves and FFR calculations may then be displayed on the Avanta™ user interface display or other console. Electrical signals may also be provided to other hemodynamic monitoring systems for additional monitoring and display.

In one exemplary application of the thrombus removal catheter 300 shown in FIG. 36, a clinical "use case" using the catheter 300 may include the steps of: (1) diagnosing a thrombus during an angiogram with support from a power injector; (2) retrieving a diagnostic catheter (if required); (3) inserting the thrombus removal catheter 300 into the patient's blood vessel V having the thrombus; (4) measuring the initial thrombus occlusion effect on blood flow; (5) beginning aspiration of the affected area using the thrombus removal catheter 300; (6) pausing aspiration; (7) measuring the remaining effect of thrombus occlusion on blood flow; (8) determining if enough thrombus has been removed; and repeating forgoing steps (5)-(8) as needed.

The various embodiments of the FFR measurement system and method in this disclosure are advantageous because a power injector is used to push fluid through a blood vessel so that adenosine and other pharmaceuticals do not have to be administered during FFR procedures. Thus, a person suspected of having heart disease does not have to receive a drug that paces the heart to the maximum possible cardiac output. Moreover, flow rate is controlled externally and the heart remains unaffected. Protocol-based fluid delivery also increases the flow rate to a plateau level each and every time, enabling maximum pressure differential and this ensures a more "correct" objective number of flow diminishment. Further, the process is an "on demand" feature because the power injector is constantly available and measurements may be taken and repeated at any time. Objective evidence is gained over time and the process may be repeated numerous times as needed.

The foregoing embodiments of the FFR measurement system and method enable Interventional Radiology (IR) clinicians to have maximum flow across a suspect region. Normally, IR clinicians would not use a vesolator dilator. In most cases, IR clinicians would refer the patient to Interventional Cardiologists (IC) clinicians, and the embodiments of the FFR measurement system and method opens FFR opportunities to IR clinicians.

Additionally, nitroglycerine and other vasodilators can still be prescribed without interference to the FFR test, and patients taking phosphodiesterase inhibitors like Viagra® do not need to come off of the drug for the testing. Further, after an initial characterization of ideal fluid flow with one medium, like contrast, additional fluid flows could be substituted with similar effect. The various embodiments described in this disclosure are further applicable to heart valve or other structural diseases. Patients with these afflictions may not be able to circulate blood at maximum hyperemia and may not benefit from current FFR techniques. Accordingly, giving the patient a vasodilator increases the pacing of the heart, but does not appreciably increase the pumping of blood.

In contrast to certain of the prior art discussed previously, the FFR measurement techniques set forth previously utilize continual flow under power injection in which flow velocity can be controlled, and pressure in the blood vessel V is measured by one or more (e.g., multiple) sensors. Additionally, in the FFR measurement techniques described previously, two pressure readings may be compared and a predetermined distance between measurement locations is not required. Further, only one fluid type, such as contrast media, is required. Moreover, the foregoing FFR measurement techniques include fluid viscosity as a consideration in the ultimate understanding of the pressure differences across the stenosis S.

Figure 37:
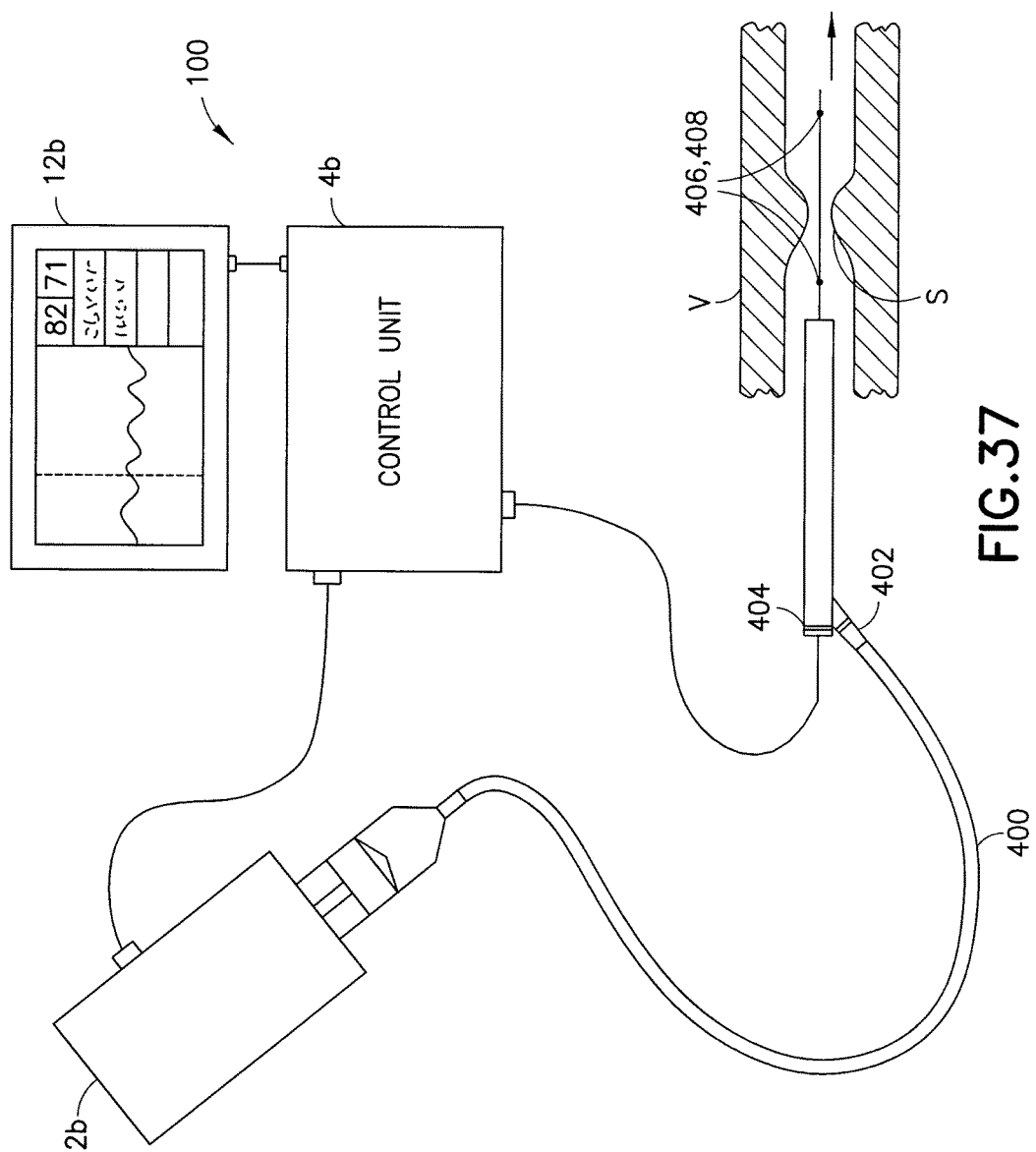
FIG. 37 is a schematic view of a fluid delivery system operable to deliver fluid flow in an optimized manner.

Referring next or FIG. 37, a fluid delivery system 10b comprising a power fluid injector 2b and a control feature or control unit 4b that enables the fluid injection system 10b to be integrated with a pressure-sensing and fluid delivery catheter 400 is shown. The fluid delivery system 10b further comprises a graphical user interface display 12b in a similar manner to that described previously in this disclosure. In the fluid delivery system 10b, the power injector 2b is integrated with the pressure catheter 400 to deliver fluid in an optimized manner based on information obtained by the pressure catheter 400. The fluid delivery system 10b may comprise a syringe-based or pump-based power injector 2b, appropriate fluid conducting lines, the microprocessor-based control unit 4b, the graphical user interface display 12b, and the pressure-sensing and fluid delivery catheter 400 (hereinafter "catheter 400"). The catheter 400 comprises multiple lumens, one lumen 402 for delivering fluid in the blood vessel V having the stenosis S, and a second lumen 404 supporting a guidewire or other structure having a single or multiple sensors 406, 408, which are typically pressure sensors in the present embodiment. Electronic communication or connection is between the pressure sensors 406, 408, and the control unit 4b either in a wired configuration as shown or via wireless connection as will be appreciated by those skilled in the art. The control unit 4b is further in electronic communication or connection with the graphical user interface display 12b and the power injector 2b as illustrated. In the depicted embodiment, the catheter 400 is placed in the blood vessel V with one sensor 408 downstream of an obstruction, such as stenosis S, and one sensor 406 is placed upstream of the stenosis S. Upon user initiation, such as by pressing a button on the graphical user interface display 12b, the fluid delivery system 10b delivers fluid, such as contrast media, via the power injector 2b within a set flow rate/range, and the control unit 4b monitors the upstream pressure via sensor 406 and increases or decreases the pressure/flow based on preprogrammed algorithms to achieve an optimum upstream pressure/flow, enabling a corresponding pressure or flow drop downstream of the stenosis S. The control unit 4b further monitors the downstream pressure via sensor 408 and the upstream pressure via sensor 406 and calculates FFR and other desired physiological parameters. The fluid delivery data stored by the control unit 4b including pressure data from the catheter 400 may be combined to provide additional information and analysis including, mean, max, integrals and profiles. The fluid delivery system 10b also provides real time data and playback capabilities in addition to summary data. The fluid delivery system 10b may be adapted to conduct fluid injections and collect readings automatically from a single user initiation, and provides fluid flow, pressure readings, and final results. Information can be stored in memory in the control unit 4b and may be linked to patient procedure information including imaging system files as well as being shared with hospital information systems (HIS). In another variation, an aspiration (suction) catheter may be placed downstream of the obstruction, such as stenosis S, and may be controlled by the control unit 4b to create the optimized negative pressure to achieve the optimized conditions and to calculate FFR and other physiological parameters.

Figure 38:
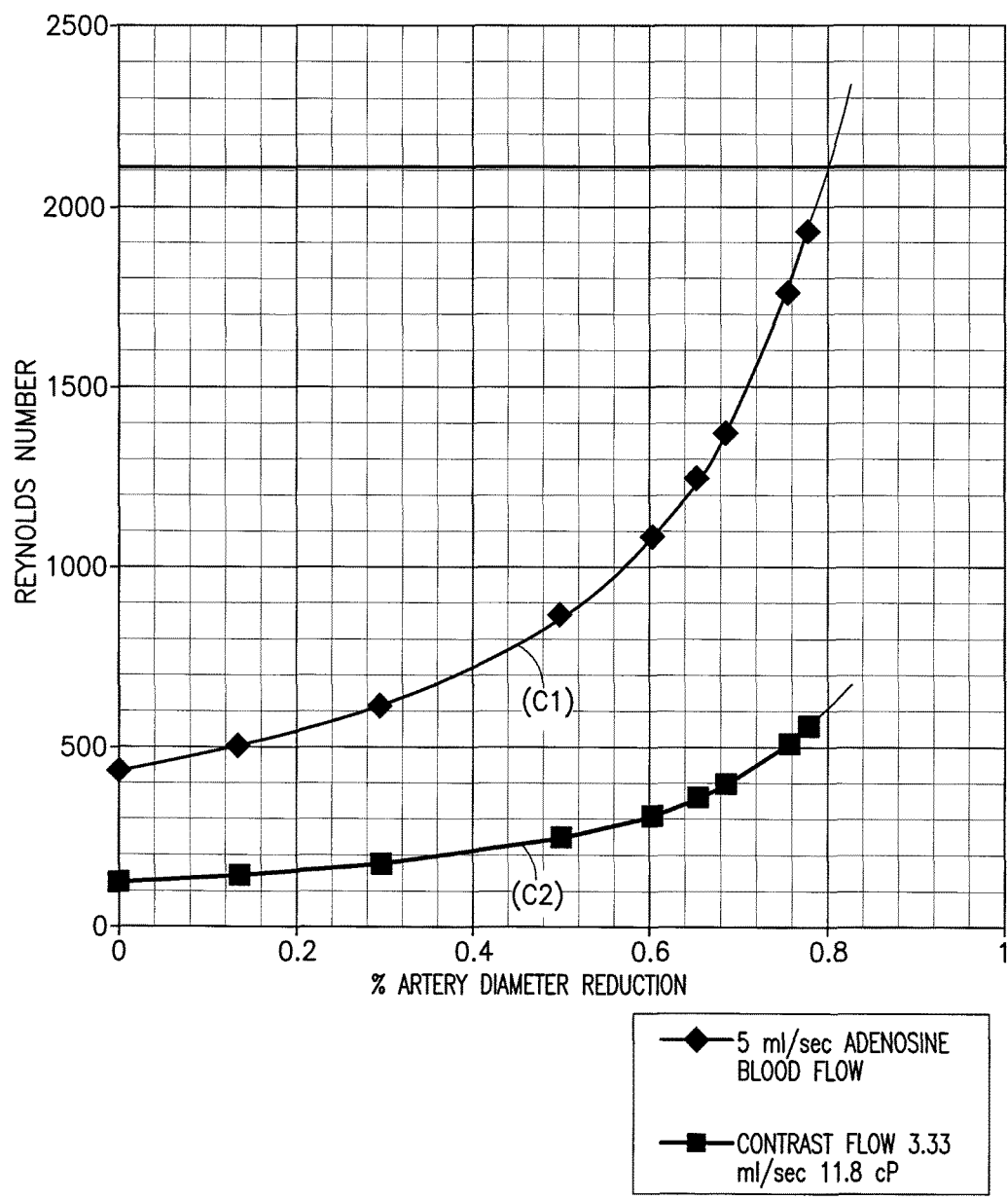
FIG. 38 is a graph of Reynolds Number vs. Artery Diameter Reduction used to describe aspects of the methods of determining FFR described herein.
Figure 39:
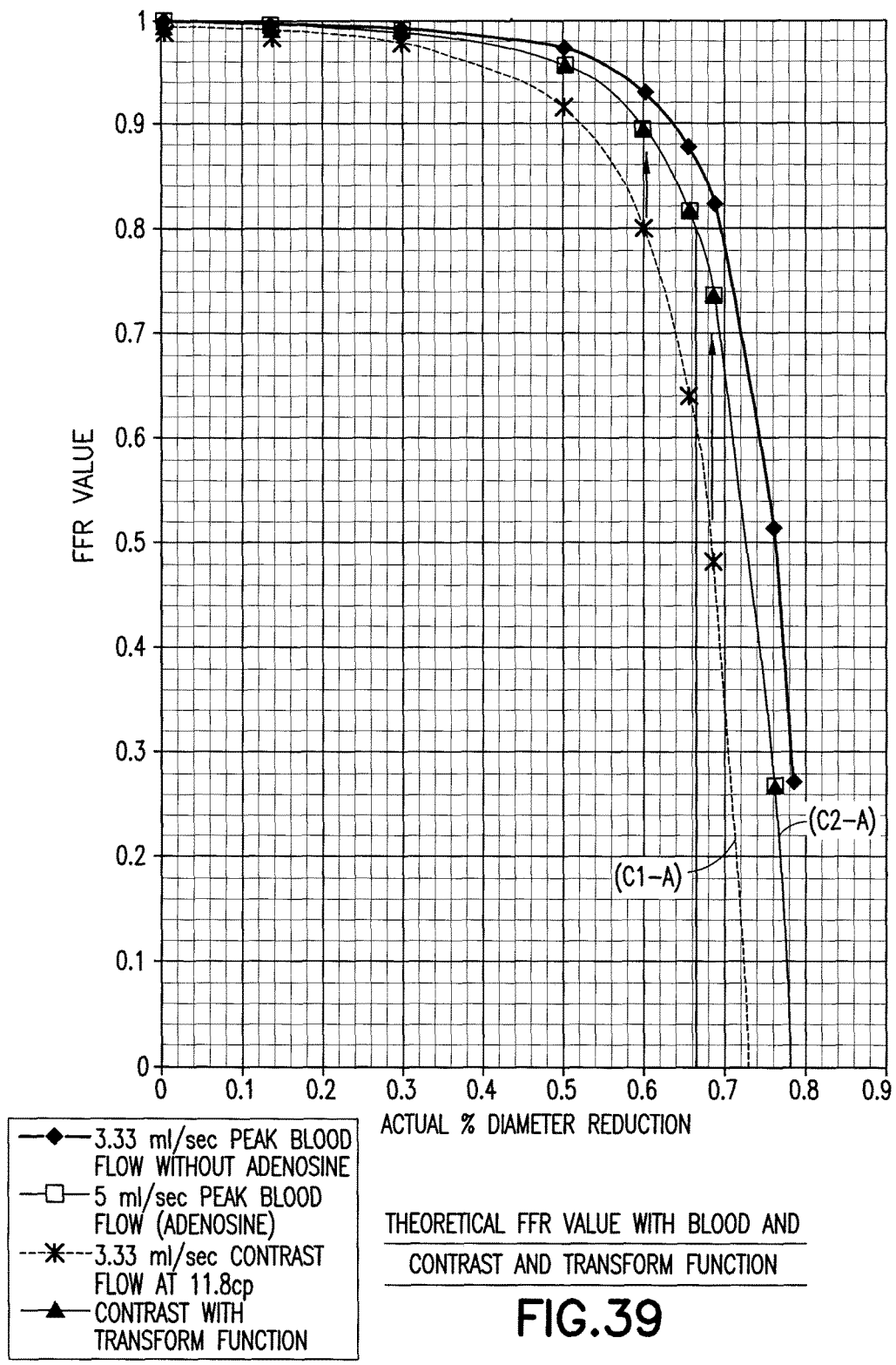
FIG. 39 is a graph of Theoretical FFR Value with Blood and Contrast Transform Function used to describe aspects of the methods of determining FFR described herein.

Referring to FIGS. 38-39, during a typical FFR interventional case, high blood flows are required to generate a pressure drop across the coronary lesion or stenosis S for cardiologists to measure and determine the extent of occlusion by determining an industry standard FFR ratio (distal pressure/proximal pressure). This high blood flow rate across a coronary lesion will have high linear blood flow velocities. This high blood flow velocity can cause turbulent flow conditions of the blood in the occluded artery. In fluid mechanics, the Reynolds number (Re) is a dimensionless number that gives a measure of the ratio of inertial forces to viscous forces. The Reynolds number is also used to characterize different flow regimes, such as laminar or turbulent flow. Laminar flow occurs at low Reynolds numbers, where viscous forces are dominant and is characterized by smooth, constant fluid motion. Turbulent flow occurs at high Reynolds numbers and is dominated by inertial forces, which tend to produce chaotic eddies, vortices, and other flow instabilities. It has experimentally been determined that turbulent flow rates cause a higher level of mechanical blood damage, also known as "hemolysis", as known from: Effects of turbulent stresses upon mechanical hemolysis: experimental and computational analysis, Kameneva M V et al. [ASAIO JOURNAL (American Society for Artificial Internal Organs). 2004 September-October; 50(5):418-23, incorporated herein by reference]. Reynolds numbers (Re) are calculated per the formula provided below. It is generally accepted that Reynolds numbers above 2100 are classified as turbulent. The Reynolds number (Re) is calculated for a flow in a pipe or tube or artery as follows:

$$Re = \frac{\rho v D_H}{\mu} = \frac{v D_H}{\nu} = \frac{Q D_H}{\nu A}$$

Where:

$D_H$ is the hydraulic diameter of the pipe; its characteristic traveled length, L, (m).

Q is the volumetric flow rate ($m^3$/s).

A is the pipe cross-sectional area ($m^2$).

v is the mean velocity of the object relative to the fluid (SI units: m/s).

$\mu$ is the dynamic viscosity of the fluid (Pa·s or N·s/$m^2$ or kg/(m·s)).

$\nu$ is the kinematic viscosity ($\nu=\mu/\rho$) ($m^2$/s).

$\rho$ is the density of the fluid (kg/$m^3$).

In the present application, Reynolds numbers were calculated for increasing artery diameter reductions and plotted as shown in FIG. 38. Two curves were generated and plotted from the calculations. The first curve (C1) was for adenosine increased arterial blood flow at 5 ml/sec in a native coronary artery of 3.9 mm with an occlusion length of 10 mm using a blood viscosity of 4 cP. The second curve (C2) was for contrast flow at 3.33 ml/sec with an artery the same as above but the contrast viscosity was 11.8 cP. As FIG. 38 shows, when plotted and compared, the contrast flow curve has lower Reynolds numbers than the adenosine blood flow curve and, thus, it can be concluded that the level of blood hemolysis will be less using the contrast based FFR techniques of the present disclosure. While the calculations do not consider the reduced flow area due to the presence of a pressure wire, the presence of a pressure wire during FFR measurements will only increase Reynolds numbers and hemolysis effects using adenosine blood flow.

Additionally, referring to FIG. 39, the contrast flow at 3.33 ml/sec in the present example produces higher pressure drops than the adenosine blood flow rate at 5 ml/sec due to the viscosity effects of the contrast and will have a more defined FFR value at lower artery diameter reductions. This contrast FFR ratio as shown by first curve (C1-A) can be transformed to the industry standard FFR value well-known to cardiologists and represented by second curve (C2-A) by simple equations as follows:

FFR Adenosine Value=(((Contrast FFR Value×−0.0492094)+0.491816)+Contrast FFR Value)

While embodiments of an FFR measurement system and method were provided in the foregoing description, those skilled in the art may make modifications and alterations to these embodiments without departing from the scope and spirit of the present disclosure. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A method of determining fractional flow reserve (FFR) in a blood vessel having a stenosis, the method comprising:

identifying a maximum flow rate through the blood vessel by injecting a fluid using a fluid delivery system proximal of the stenosis until retrograde flow of the fluid is observed;

measuring with an at least one pressure sensor a first pressure in the blood vessel proximal of the stenosis and a second pressure in the blood vessel distal of the stenosis during the injecting of the fluid at the maximum flow rate;

measuring a first pressure drop across the stenosis based on the first pressure and the second pressure using the fluid delivery system; and calculating a first FFR from the first pressure drop using the fluid delivery system.

2. The method of claim 1, wherein the measuring of the first pressure comprises placing the at least one pressure sensor proximal of the stenosis, and wherein the measuring of the second pressure comprises placing the at least one pressure sensor distal of the stenosis.

3. The method of claim 1, wherein the injecting of the fluid using the fluid delivery system is reduced or discontinued after a preset period of time.

4. The method of claim 1, wherein the measuring of the first pressure drop across the stenosis comprises calculating a ratio of the second pressure to the first pressure.

5. The method of claim 1, wherein the first pressure and the second pressure are measured simultaneously.

6. The method of claim 1, further comprising validating the first FFR using the fluid delivery system.

7. The method of claim 6, wherein the validating of the first FFR comprises:

reinjecting the fluid using the fluid delivery system at the maximum flow rate;

measuring with the at least one pressure sensor a third pressure in the blood vessel distal of the stenosis and a fourth pressure in the blood vessel proximal of the stenosis during the reinjecting of the fluid;

measuring a second pressure drop across the stenosis based on the third pressure and the fourth pressure using the fluid delivery system; and calculating a second FFR from the second pressure drop using the fluid delivery system.

8. The method of claim 7, wherein the measuring of the third pressure comprises placing the at least one pressure sensor distal of the stenosis, and wherein the measuring of the fourth pressure comprises placing the at least one pressure sensor proximal of the stenosis.

9. The method of claim 7, wherein the measuring of the second pressure drop across the stenosis comprises calculating a ratio of the third pressure to the fourth pressure.

10. The method of claim 7, further comprising filtering with the fluid delivery system the third pressure and the fourth pressure to exclude mean arterial pressure.

11. The method of claim 1, wherein a flow rate of the fluid injected into the blood vessel is controlled by the fluid delivery system.

12. The method of claim 1, wherein a pressure of the fluid injected into the blood vessel is controlled by the fluid delivery system.

13. The method of claim 1, wherein the injected fluid comprises a contrast medium.

14. A method of determining fractional flow reserve (FFR) in a blood vessel having a stenosis, the method comprising:

inserting a multi-lumen catheter into the blood vessel;

identifying a maximum flow rate through the blood vessel by injecting a fluid using a fluid delivery system proximal of the stenosis until a retrograde flow of the fluid is observed;

measuring a first pressure in the blood vessel proximal of the stenosis and a second pressure in the blood vessel distal of the stenosis during injecting of the fluid at the maximum flow rate;

measuring a first pressure drop across the stenosis based on the first pressure and the second pressure using the fluid delivery system;

reducing or discontinuing the injecting of the fluid when the retrograde flow is present in the blood vessel; and calculating a first FFR from the first pressure drop using the fluid delivery system.

15. The method of claim 14, wherein the injecting of the fluid using the fluid delivery system is reduced or discontinued after a preset period of time.

16. The method of claim 14, wherein the measuring of the first pressure drop across the stenosis comprises calculating a ratio of the second pressure to the first pressure.

17. The method of claim 14, wherein the first pressure and the second pressure are measured simultaneously using an at least one pressure sensor and a hemodynamic monitoring port on the multi-lumen catheter.

18. The method of claim 14, further comprising validating the first FFR using the fluid delivery system, wherein the validating of the first FFR comprises:

reinjecting the fluid using the fluid delivery system at the maximum flow rate;

measuring a third pressure in the blood vessel distal of the stenosis and a fourth pressure in the blood vessel proximal of the stenosis during the reinjecting of the fluid;

measuring a second pressure drop across the stenosis based on the third pressure and the fourth pressure using the fluid delivery system; and calculating a second FFR from the second pressure drop using the fluid delivery system.

19. The method of claim 18, wherein the measuring of the second pressure drop across the stenosis comprises calculating a ratio of the third pressure to the fourth pressure.

20. The method of claim 14, wherein the multi-lumen catheter comprises at least a fluid injecting lumen and a hemodynamic monitoring lumen.

* * * * *

UNITED STATES PATENT AND TRADEMARK OFFICE
CERTIFICATE OF CORRECTION

PATENT NO. : 9,931,041 B2
APPLICATION NO. : 15/482947
DATED : April 3, 2018
INVENTOR(S) : Riley et al.

Page 1 of 1

It is certified that error appears in the above-identified patent and that said Letters Patent is hereby corrected as shown below:

On the Title Page

In Item (74), under "Attorney, Agent, or Firm", in Column 2, Line 1, delete "James L. Kent;" and insert -- Joseph L. Kent; --, therefor.

In the Specification

In Column 1, Line 34, delete "angioplasty" and insert -- coronary angioplasty --, therefor.
In Column 1, Line 38, delete "angioplasty" and insert -- coronary angioplasty --, therefor.
In Column 1, Line 52, delete "qualitative" and insert -- quantitative --, therefor.
In Column 8, Line 15, delete "Darcy-Weishbach:" and insert -- Darcy-Weisbach: --, therefor.
In Column 14, Lines 51-52, delete "pressure sensors may be removed 104." and insert -- pressure sensors 104 may be removed. --, therefor.
In Column 17, Line 17, delete "vesolator" and insert -- vasodilator --, therefor.

Signed and Sealed this
Thirty-first Day of July, 2018

Andrei Iancu
*Director of the United States Patent and Trademark Office*